United States Patent
Bao et al.

(10) Patent No.: US 10,434,097 B1
(45) Date of Patent: Oct. 8, 2019

(54) METHODS AND COMPOSITIONS FOR TREATING HEARING DISORDERS

(71) Applicant: GATEWAY BIOTECHNOLOGY, INC., Rootstown, OH (US)

(72) Inventors: Jianxin Bao, Kent, OH (US); Xiaojie Chen, San Francisco, CA (US)

(73) Assignee: GATEWAY BIOTECHNOLOGY, INC., Rootstown, OH (US)

( * ) Notice: Subject to any disclaimer, the term of this patent is extended or adjusted under 35 U.S.C. 154(b) by 88 days.

(21) Appl. No.: 15/423,485

(22) Filed: Feb. 2, 2017

Related U.S. Application Data

(63) Continuation of application No. 15/265,302, filed on Sep. 14, 2016, now abandoned.

(60) Provisional application No. 62/218,483, filed on Sep. 14, 2015.

(51) Int. Cl.
| | |
|---|---|
| *A61K 31/4745* | (2006.01) |
| *A61K 36/59* | (2006.01) |
| *A61K 45/06* | (2006.01) |
| *A61K 9/00* | (2006.01) |
| *A61K 31/13* | (2006.01) |
| *A61K 31/138* | (2006.01) |
| *A61K 31/4985* | (2006.01) |
| *A61K 31/5375* | (2006.01) |
| *A61K 31/423* | (2006.01) |

(52) U.S. Cl.
CPC ........ *A61K 31/4745* (2013.01); *A61K 9/0019* (2013.01); *A61K 9/0046* (2013.01); *A61K 31/13* (2013.01); *A61K 31/138* (2013.01); *A61K 31/423* (2013.01); *A61K 31/4985* (2013.01); *A61K 31/5375* (2013.01); *A61K 36/59* (2013.01); *A61K 45/06* (2013.01)

(58) Field of Classification Search
CPC .. A61K 31/4745; A61K 31/13; A61K 31/138; A61K 31/423; A61K 31/4985; A61K 31/5375; A61K 9/0019; A61K 9/0046
See application file for complete search history.

(56) References Cited

U.S. PATENT DOCUMENTS

| | | |
|---|---|---|
| 2004/0214753 A1 | 10/2004 | Britten et al. |
| 2007/0021352 A1 | 1/2007 | Anderson et al. |

OTHER PUBLICATIONS

Chen, et al. The Potential of Tetrandrine as a Protective Agent for Ischemic Stroke. Molecules 2011, 16(9), 8020-8032; doi:10.3390/molecules16098020.

(Continued)

*Primary Examiner* — Yong S. Chong
(74) *Attorney, Agent, or Firm* — Wilson Sonsini Goodrich & Rosati, P.C.

(57) ABSTRACT

Disclosed herein are pharmaceuticals, compositions, kits, and methods for treating or preventing a hearing disorder in a subject in need thereof, wherein the pharmaceuticals, compositions, kits, and methods comprise administering a therapeutically effective amount of tetrandrine (TET) or a salt thereof.

45 Claims, 16 Drawing Sheets

(56) References Cited

OTHER PUBLICATIONS

Gao, et al. Tetrandrine exerts antidepressant-like effects in animal models: role of brain-derived neurotrophic factor. Behav Brain Res. Feb. 1, 2013;238:79-85. doi: 10.1016/j.bbr.2012.10.015. Epub Oct. 22, 2012.

Jin, et al. Tetrandrine Cytotoxicity and Its Dual Effect on Oxidative Stress-Induced Apoptosis Through Modulating Cellular Redox States in Neuro 2a Mouse Neuroblastoma Cells. Life Sci 71 (17), 2053-2066. Sep. 13, 2002.

Kobayashi, et al. Inhibitory effects of tetrandrine on angiogenesis in adjuvant-induced chronic inflammation and tube formation of vascular endothelial cells. Biol Pharm Bull. Apr. 1998;21(4):346-9.

Koh, et al. Protective effects of fangchinoline and tetrandrine on hydrogen peroxide-induced oxidative neuronal cell damage in cultured rat cerebellar granule cells. Planta Med. Jun. 2003;69(6):506-12.

Lin, et al. Anti-nociceptive, anti-inflammatory and toxicological evaluation of Fang-Ji-Huang-Qi-Tang in rodents. BMC Complement Altern Med. 2015; 15: 10. Published online Feb. 5, 2015 doi: 10.1186/s12906-015-0527-5.

Liu, et al. Effects of tetrandrine on cytosolic free calcium concentration in corpus cavernosum smooth muscle cells of rabbits. Asian J Androl. Jul. 2006;8(4):405-9.

Sakurai, et al. Two pore channels control Ebolavirus host cell entry and are drug targets for disease treatment. Science. Feb. 27, 2015; 347(6225): 995-998. doi: 10.1126/science.1258758.

Shen, et al. Tetrandrine ameliorates ischaemia-reperfusion injury of rat myocardium through inhibition of neutrophil priming and activation. Br J Pharmacol. Dec. 1999; 128(7): 1593-1601. doi: 10.1038/sj.bjp.0702958.

Shine, et al. Ameliorative effect of alkaloid extract of Cyclea peltata (Poir.) Hook. f. & Thoms. roots (ACP) on APAP/CCI4 induced liver toxicity in Wistar rats and in vitro free radical scavenging property. Asian Pac J Trop Biomed. Feb. 2014;4(2):143-51. doi: 10.1016/S2221-1691(14)60223-9.

Slater, et al. Effects of the plant alkaloid tetrandrine on human nicotinic acetylcholine receptors. Eur J Pharmacol. Aug. 30, 2002;450(3):213-21.

Wang, et al. Effect of tetrandrine on calcium-dependent tumour necrosis factor-alpha production in glia-neurone mixed cultures. Basic Clin Pharmacol Toxicol. Oct. 2005;97(4):244-8.

Wong, et al. Comparative effects of tetrandrine and berbamine on subcutaneous air pouch inflammation induced by interleukin-1, tumour necrosis factor and platelet-activating factor. Agents Actions. May 1992;36(1-2):112-8.

Xie, et al. Pharmacological Actions of Tetrandrine in Inflammatory Pulmonary Diseases. Acta Pharmacol Sin 23 (12), 1107-1113. 12, 2002.

Yao, et al. Effects of tetrandrine on cardiovascular electrophysiologic properties. Acta Pharmacol Sin. Dec. 2002;23(12):1069-74.

TET effects on mouse avoidance test. C57BL/6J mice were trained to move in the shuttle box when a sound was present. After 10 days of training, the latency of their avoidance test was recored and compared between the control (0) and drug-treated groups. Data are shown as means +/- S.E.M. * $P < 0.05$ compared with the control group.

TET prophylactic effects against NIHL in chinchillas. ABR thresholds were determined one day before, one day after (TTS), and two weeks after (PTS) the noise exposure. TET at 60 mg/kg was administrated (i.p.) two hours before the noise exposure. The threshold shifts are shown as means +/- S.E.M.

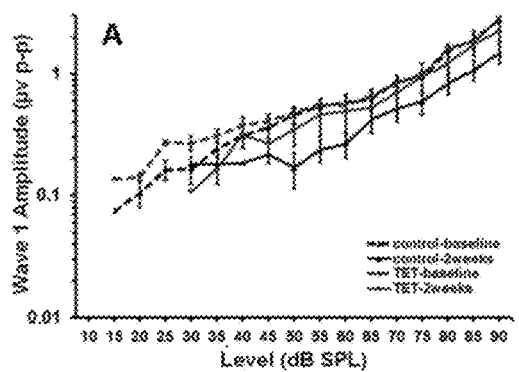
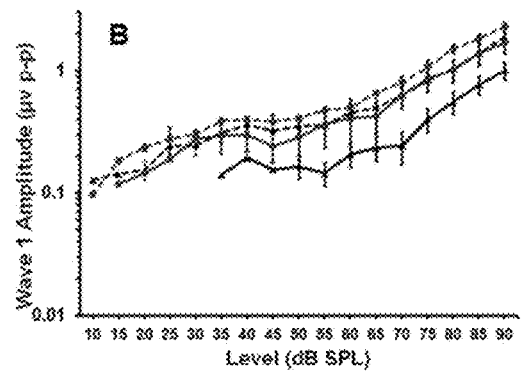
Figure 12A
Figure 12B
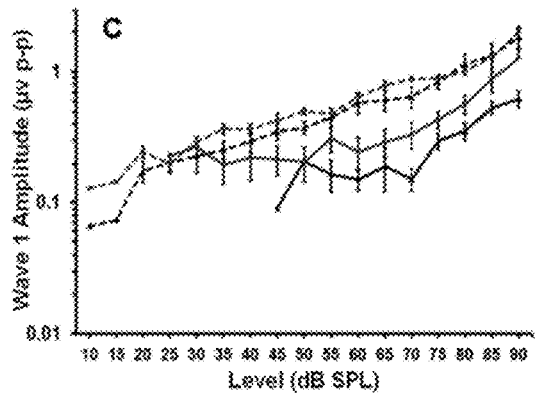
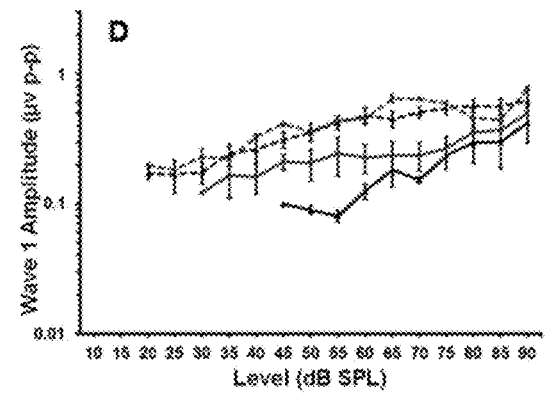
Figure 12C
Figure 12D

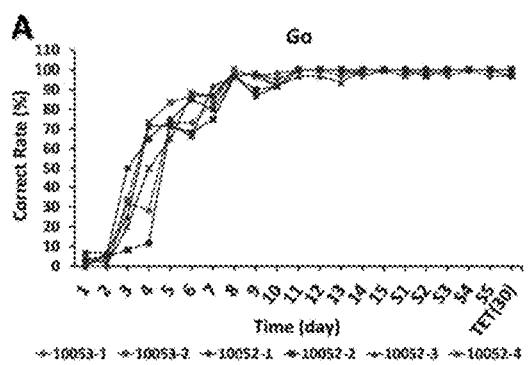
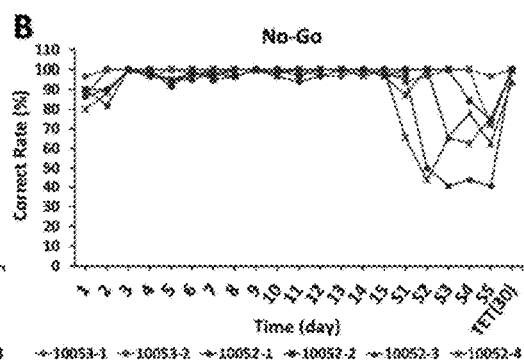
Figure 15A                Figure 15B
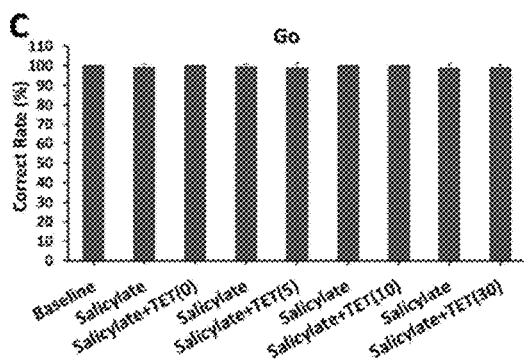
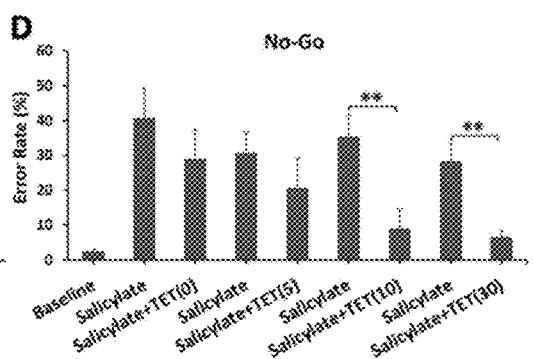
Figure 15C                Figure 15D

METHODS AND COMPOSITIONS FOR TREATING HEARING DISORDERS

CROSS-REFERENCE

This application is a continuation of U.S. application Ser. No. 15/265,302, filed on Sep. 14, 2016, which claims the benefit of U.S. Provisional Application No. 62/218,483, filed Sep. 14, 2015, which applications are incorporated herein by reference in their entirety.

BACKGROUND

Hearing disorders such as noise-induced hearing loss (NIHL), age-related hearing loss (ARHL), hearing loss due to ototoxic drugs or injury, and tinnitus are a growing health problem, with varied and complex etiology. While some forms of hearing disorders are clearly genetic in origin, others are either wholly or at least partially environmental in nature. There is a need for pharmaceuticals, compositions, and methods for the prevention and/or treatment of hearing disorders. For example, there is a need for pharmaceuticals, compositions and methods of reducing, ameliorating, and/or counteracting one or more symptoms of tinnitus, NIHL, ARHL or presbycusis, or hearing loss due to drugs or injury.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

SUMMARY OF THE INVENTION

Disclosed herein are pharmaceuticals, compositions, kits, and methods for the prevention and/or treatment of hearing loss, for example, by administering a therapeutically effective amount of tetrandrine (TET) or a salt thereof.

In one aspect, disclosed herein is a method for treating or preventing a hearing disorder in a subject in need thereof comprising administering a therapeutically effective amount of tetrandrine (TET) or a salt thereof. In some cases, the subject is a human. In some cases, the subject is suffering from the hearing disorder. In some cases, the method treats the hearing disorder. In some cases, the subject is at risk of developing the hearing disorder. In some cases, the subject is diagnosed with the hearing disorder. In some cases, the method prevents the hearing disorder. In some cases, the method delays onset of the hearing disorder. In some cases, the therapeutically effective amount of TET or salt thereof is administered orally, auricularly, intratympanically, buccally, intravenously, parenterally, rectally, intradermally, transdermally, pulmonary, nasally, topically, or by inhalation spray. In some cases, the therapeutically effective amount of TET or salt thereof is administered auricularly. In some cases, the auricular administration is an injection.

In some cases, the auricular administration is an eardrop. In some cases, the therapeutically effective amount of TET or salt thereof is at least about 1 µg of TET or salt thereof per kg of the subject. In some cases, the therapeutically effective amount of TET or salt thereof is less than about 1000 mg of TET or salt thereof per kg of the subject. In some cases, the therapeutically effective amount of TET or salt thereof is from about 1 µg to about 1000 mg of TET or salt thereof per kg of the subject. In some cases, the therapeutically effective amount of TET or salt thereof is comprised in a pharmaceutical composition. In some cases, the therapeutically effective amount of TET or salt thereof is in a unit dosage form. In some cases, the unit dosage form is administered at least once a day, twice a day, or three times a day. In some cases, the unit dosage form is administered for at least one day, at least two days, at least three days, at least four days, at least five days, at least six days, at least one week, at least two weeks, at least three weeks, at least four weeks, at least one month, at least two months, at least six months, or at least one year. In some cases, the unit dosage form is administered intermittently. In some cases, the unit dosage form is administered continuously. In some cases, the unit dosage form is in a tablet, capsule, caplet, gel cap, powder, or solution dosage form. In some cases, the tablet, capsule, caplet, gel cap, powder, or solution dosage form has a unit weight of at least about 10 mg. In some cases, the tablet, capsule, caplet, gel cap, powder, or solution dosage form has a unit weight of less than about 10 g. In some cases, the tablet, capsule, caplet, gel cap, powder, or solution dosage form has a unit weight of from about 10 mg to about 10 g. In some cases, the therapeutically effective amount of TET or salt thereof is in a solution dosage form. In some cases, the solution dosage form has a unit volume of at least about 1 mL. In some cases, the solution dosage form has a unit volume of less than about 500 mL. In some cases, the solution dosage form has a unit volume of from about 1 mL to about 500 mL. In some cases, the therapeutically effective amount of TET or salt thereof is in a powder dosage form. In some cases, the method further comprises mixing a sterile solution with the powder dosage form prior to the administration of the therapeutically effective amount of TET or salt thereof.

In some cases, the therapeutically effective amount of TET or salt thereof is administered at least about 12 hours before occurrence of the hearing disorder or an event that initiates the hearing disorder. In some cases, the therapeutically effective amount of TET or salt thereof is administered less than about 10 days before occurrence of the hearing disorder or an event that initiates the hearing disorder. In some cases, the therapeutically effective amount of TET or salt thereof is administered at least about 12 hours after occurrence of the hearing disorder or an event that initiates the hearing disorder. In some cases, the therapeutically effective amount of TET or salt thereof is administered less than about 10 days after occurrence of the hearing disorder or an event that initiates the hearing disorder.

In some cases, the hearing disorder in the subject in need thereof is noise-induced hearing loss (NIHL). In some cases, the hearing disorder in the subject in need thereof is age-related hearing loss (ARHL) or presbycusis. In some cases, the hearing disorder in the subject in need thereof is injury-induced hearing loss. In some cases, the hearing disorder in the subject in need thereof is drug-induced hearing loss. In some cases, the hearing disorder in the subject in need thereof is tinnitus. In some cases, the drug-induced hearing loss is caused by an ototoxic drug or a salt thereof. In some cases, the ototoxic drug or salt thereof comprises a chemotherapeutic agent, an antineoplastic agent, an antibiotic, a loop-diuretic, a quinine or quinine-like compound, a salicylate or salicylate-like compound, a salt of any of these, or any combination thereof. In some cases, the ototoxic drug or salt thereof is an antibiotic or salt thereof, wherein the antibiotic or salt thereof is not streptomycin or a salt thereof.

In some cases, the therapeutically effective amount of TET or salt thereof is in a supplement product. In some cases, the therapeutically effective amount of TET or salt thereof is comprised in an herb extract. In some cases, the herb is *Stephania tetrandra*. In some cases, the herb is *Stephania tetrandra* S Moore. In some cases, the therapeutically effective amount of TET or salt thereof is isolated and purified. In some cases, the therapeutically effective amount of TET or salt thereof is a diastereoisomer having a diastereomeric excess of at least about 50%, at least about 60%, at least about 70%, at least about 80%, at least about 85%, at least about 90%, at least about 95%, or from at least about 50% to about 100%.

In another aspect, disclosed herein is a pharmaceutical composition comprising a therapeutically effective amount of TET or a salt thereof. In some cases, the pharmaceutical composition further comprises an active pharmaceutical ingredient (API) or a salt thereof. In some cases, the API or salt thereof comprises an antioxidant, a spin-trapping agent, a N-methyl-D-aspartate (NMDA) antagonist, a selective serotonin reuptake inhibitor (SSRI), a dopamine releasing agent (DRA), an acetylcholine release inducer, a norepinephrine reuptake inhibitor (NERI), a monamineoxidase-A inhibitor (MAI), a serotonin reuptake inhibitor (SRI), a serotonin-norepinephrine reuptake inhibitor (SNRI), a calcium channel blocker (CCB), a norepinephrine selective reuptake inhibitor (NSRI), a 5HT serotonin reuptake inhibitor (5HT SRI), zonisamide, gabapentin, a cannabinoid, a salt of any of these, or any combination thereof. In some cases, the API or salt thereof comprises an antioxidant, a spin-trapping agent, a salt of any of these, or any combination thereof. In some cases, the API or salt thereof comprises allopurinol, glutathione, L-carnitine, methionine, a salt of any of these, or any combination thereof. In some cases, the API or salt thereof comprises a NMDA antagonist or a salt thereof. In some cases, the API or salt thereof comprises riluzole, caroverine, memantine, magnesium, a salt of any of these, or any combination thereof. In some cases, the API or salt thereof comprises a SSRI or a salt thereof. In some cases, the API or salt thereof comprises fluoxetine, sertraline, S-citalopram, alaproclate, a salt of any of these, or any combination thereof. In some cases, the API or salt thereof comprises a DRA or a salt thereof. In some cases, the API or salt thereof comprises amantadine or a salt thereof. In some cases, the API or salt thereof comprises an acetylcholine release inducer, a NERI, a salt of any of these, or any combination thereof. In some cases, the API or salt thereof comprises bifemelane or a salt thereof. In some cases, the API or salt thereof comprises a MAI, a SRI, a salt of any of these, or any combination thereof. In some cases, the API or salt thereof comprises pirlindole or a salt thereof. In some cases, the API or salt thereof comprises a SNRI or a salt thereof. In some cases, the API or salt thereof comprises milnacipran, bicifadine, a salt of any of these, or any combination thereof. In some cases, the API or salt thereof comprises a CCB or a salt thereof. In some cases, the API or salt thereof comprises nimodipine, verapamil, a salt of any of these, or any combination thereof. In some cases, the API or salt thereof comprises a NSRI or a salt thereof. In some cases, the API or salt thereof comprises atomoxetine or a salt thereof. In some cases, the API or salt thereof comprises a 5HT SRI or a salt thereof. In some cases, the API or salt thereof comprises indeloxazine or a salt thereof. In some cases, the API or salt thereof comprises zonisamide or a salt thereof. In some cases, the pharmaceutical composition comprises the therapeutically effective amount of TET. In some cases, the pharmaceutical composition comprises a salt of the therapeutically effective amount of TET.

In some cases, the therapeutically effective amount of TET or salt thereof is at least about 1 of TET or salt thereof per kg of the subject. In some cases, the therapeutically effective amount of TET or salt thereof is less than about 1000 mg of TET or salt thereof per kg of the subject. In some cases, the therapeutically effective amount of TET or salt thereof is from about 1 µg to about 1000 mg of TET or salt thereof per kg of the subject. In some cases, the therapeutically effective amount of TET or salt thereof is in a unit dosage form. In some cases, the unit dosage form is in a tablet, capsule, caplet, gel cap, powder, or solution dosage form. In some cases, the tablet, capsule, caplet, gel cap, powder, or solution dosage form has a unit weight of at least about 10 mg. In some cases, the tablet, capsule, caplet, gel cap, powder, or solution dosage form has a unit weight of less than about 10 g. In some cases, the tablet, capsule, caplet, gel cap, powder, or solution dosage form has a unit weight of from about 10 mg to about 10 g. In some cases, the therapeutically effective amount of TET or salt thereof is in a solution dosage form. In some cases, the solution dosage form has a unit volume of at least about 1 mL. In some cases, the solution dosage form has a unit volume of less than about 500 mL. In some cases, the solution dosage form has a unit volume of from about 1 mL to about 500 mL. In some cases, the therapeutically effective amount of TET or salt thereof is in a supplement product. In some cases, the therapeutically effective amount of TET or salt thereof is comprised in an herb extract. In some cases, the herb is *Stephania tetrandra*. In some cases, the herb is *Stephania tetrandra* S Moore. In some cases, the therapeutically effective amount of TET or salt thereof is isolated and purified. In some cases, the therapeutically effective amount of TET or salt thereof is a diastereoisomer having a diastereomeric excess of at least about 50%, at least about 60%, at least about 70%, at least about 80%, at least about 85%, at least about 90%, at least about 95%, or from at least about 50% to about 100%.

In some cases, the pharmaceutical composition further comprises one or more therapeutically acceptable carriers. In some cases, the one or more therapeutically acceptable carriers comprise a coating material. In some cases, the coating material comprises a cellulose polymer, a plasticizer, a pigment, a colorant, a glidant, a stabilization agent, a pore former, a surfactant, or any combination thereof. In some cases, the one or more therapeutically acceptable carriers comprise a therapeutically acceptable excipient. In some cases, the therapeutically acceptable excipient comprises a diluent, a binder, a lubricant, a disintegrant, a colorant, a stabilizer, a surfactant, or any combination thereof.

In another aspect, disclosed herein is a method for treating or preventing a hearing loss in a subject in need thereof comprising administering the pharmaceutical composition described herein. In some cases, the therapeutically effective amount of TET or salt thereof is administered orally, auricularly, intratympanically, buccally, intravenously, parenterally, rectally, intradermally, transdermally, pulmonary, nasally, topically, or by inhalation spray. In some cases, the therapeutically effective amount of TET or salt thereof and the API or salt thereof are administered concurrently. In some cases, the therapeutically effective amount of TET or salt thereof and the API or salt thereof are administered consecutively. In some cases, the API or salt thereof is administered in a different route as the therapeutically effective amount of TET or salt thereof.

In another aspect, disclosed herein is a kit comprising the pharmaceutical composition described herein. In some cases, the kit is for treating or preventing a hearing loss in a subject in need thereof. In some cases, the API or salt thereof is in a same unit dosage form as the therapeutically effective amount of TET or salt thereof. In some cases, the API or salt thereof is in a separate unit dosage form from the therapeutically effective amount of TET or salt thereof. In some cases, the kit further comprises a written instruction for use. In some cases, the written instruction is for treating or preventing a hearing loss. In some cases, the written instruction is for treating or preventing a hearing loss using TET or salt thereof.

In another aspect, disclosed herein is a method of making a kit comprising manufacturing the kit described herein. In another aspect, disclosed herein is a method of making a pharmaceutical composition comprising including the therapeutically effective amount of TET or salt thereof in the pharmaceutical composition described herein. In another aspect, disclosed herein is a method of making a pharmaceutical composition, comprising contacting the therapeutically effective amount of TET or salt thereof with a therapeutically acceptable excipient. In another aspect, disclosed herein is a method for increasing motor coordination in a subject in need thereof comprising administering pharmaceutical composition described herein. In another aspect, disclosed herein is a method for improving memory in a subject in need thereof comprising administering the pharmaceutical composition described herein. In some cases, the therapeutically effective amount of TET or salt thereof is isolated and purified. In yet another aspect, disclosed herein is a supplement composition comprising a supplement amount of TET or a salt thereof. In some cases, the supplement amount of TET or a salt thereof is isolated and purified.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

(FIG. 9A). Effect of TET at Day 1; (FIG. 9B). Effect of TET on PTS measured at Day 15. The TET120 had lower threshold shifts than the control and TET80 groups at Day 1. PTS in the TET100 and TET120 groups were significantly lower than those in the control groups. Values are means±SEM. (n=7-8 per group). (*$p<0.05$, **$p<0.01$, compared to control, two-way ANOVA test).

(FIG. 10A). Effect of TET at Day 1; (FIG. 10B). Effect of TET on PTS. Both the prevention and treatment groups had significantly lower threshold shifts than the control group at Day 1. The prevent group had significantly lower PTS than the control and treatment groups. Values are means±SEM. (n=7-8 per group). (*$p<0.05$, **$p<0.01$, compared to control, two-way ANOVA).

FIGS. 12A, 12B, 12C, and 12D illustrate the mouse ABR wave-1 amplitudes of control and TET prevent groups before and at Day 15 after noise exposure at (FIG. 12A) 10 kHz. (FIG. 12B) 20 kHz. (FIG. 12C) 28.3 kHz. (FIG. 12D) 40 kHz. No group differences were detected between pre-exposure amplitudes. Day 15, the TET prevent group had higher amplitudes at each frequency at the 50-60 and 70-90 dB SPL stimulus levels. Values are means±SEM. (n=7-8 per group). (control-baseline: dotted line/triangle; control-2 weeks: solid line/triangle; TET-baseline: dotted line/circle; TET-2 weeks: solid line/circle).

(FIG. 13A) OHC loss in the control group; (FIG. 13B) OHC loss in the TET prevention group; (FIG. 13C) IHC ribbon synapses in the control group; (FIG. 13D) IHC ribbon synapses in the TET prevention group.

(FIG. 14A) Proportions of OHC survival. (FIG. 14B) Proportions of IHC synaptic ribbon survival. Values are mean±SEM. (n=5-6 per group). The TET prevent group had significantly more surviving OHCs and intact IHC ribbon synapses at the cochlear regions tuned to 10, 20, 28.3, and 40 kHz. (*p<0.05, **p<0.01, compared to control, two-way ANOVA).

FIGS. 15A, 15B, 15C, and 15D illustrate that TET diminished tinnitus-like behavior in the salicylate model. FIG. 15A: Go correct rate for both male and female mice. FIG. 15B: No-Go correct rate for both male and female mice. FIG. 15C: No significant changes for the "Go" testing either before or after drug injections, indicating that salicylate and TET have no obvious effects on motor, motivation or memory functions at these dosages. FIG. 15D: TET significantly decreased behavioral indications of tinnitus at a dosage of 10 and 30 mg/kg, but no significant changes were observed at a 5 mg/kg dosage, a positive dose effect correlation. Paired t test was used for statistical analysis. Compared with Baseline, **P<0.01.

FIG. 16A: Go correct rate for TET (60 mg/kg) group mice. FIG. 16B: No-Go correct rate for TET (60 mg/kg) group mice. FIG. 16C: No significant changes were observed for the "Go" trials. FIG. 16D: TET significantly decreased behavioral indications of tinnitus at a dosage of 60 and 90 mg/kg, but no significant changes were observed at a 30 mg/kg dosage, another positive dose effect correlation. Paired t test was used for statistical analysis. Compared with Baseline, *P<0.05, **P<0.01; compared with 8w post noise, #P<0.05, ##P<0.01.

DETAILED DESCRIPTION OF THE DISCLOSURE

Figure 1:
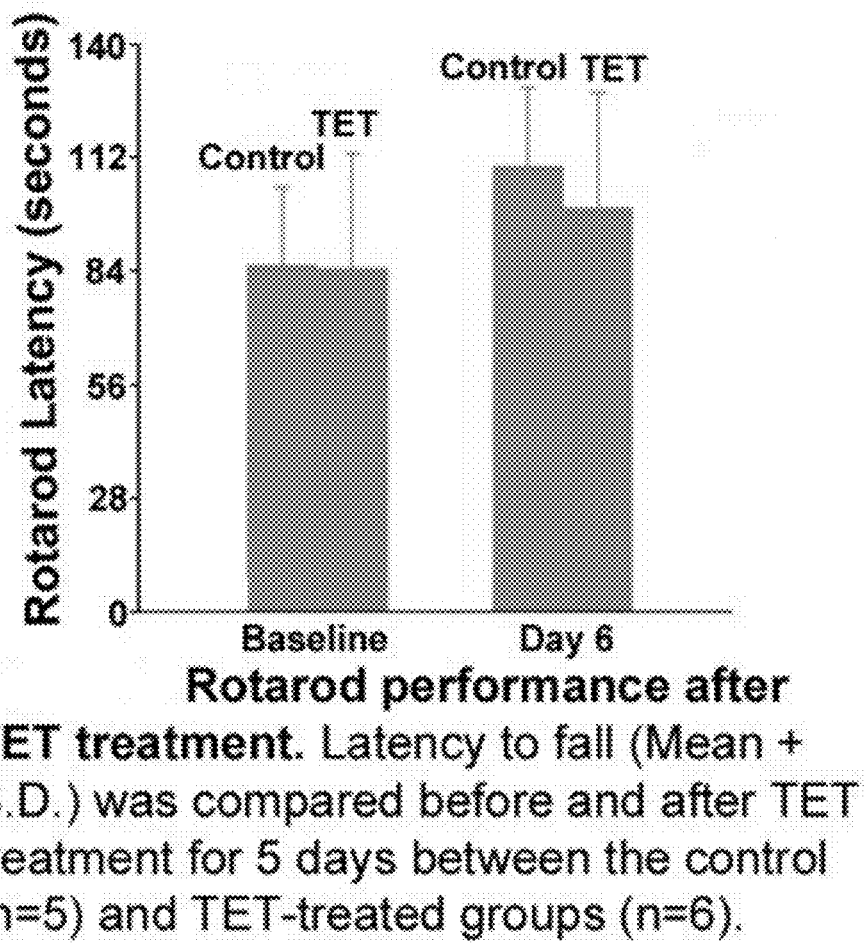
FIG. 1 is a comparison of the rotarod latency to fall between the control and TET-treated groups. Latency to fall (mean+S.D.) was compared before and after TET treatment for 5 days between the control (n=5) and TET-treated groups (n=6).

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

a. Definitions

Unless defined otherwise, all technical and scientific terms used herein have the same meaning as commonly understood by one of the ordinary skill in the art to which this invention belongs. Although any methods and materials similar or equivalent to those described herein can be used in the practice or testing of the formulations or unit doses herein, some methods and materials are now described. Unless mentioned otherwise, the techniques employed or contemplated herein are standard methodologies. The materials, methods and examples are illustrative only and not limiting.

The term "about" and its grammatical equivalents in relation to a reference numerical value and its grammatical equivalents as used herein can include a range of values plus or minus 10% from that value. For example, the amount "about 10" includes amounts from 9 to 11. The term "about" in relation to a reference numerical value can also include a range of values plus or minus 10%, 9%, 8%, 7%, 6%, 5%, 4%, 3%, 2%, or 1% from that value.

The term "hearing disorder" and its grammatical equivalents as used herein is used interchangeably to include NIHL, ARHL, tinnitus, and hearing loss due to drugs or injury.

The details of one or more inventive embodiments are set forth in the accompanying drawings, the claims, and the description herein. Other features, objects, and advantages of the inventive embodiments disclosed and contemplated herein can be combined with any other embodiment unless explicitly excluded.

Unless otherwise indicated, open terms for example "contain," "containing," "include," "including," and the like mean comprising.

The singular forms "a", "an", and "the" are used herein to include plural references unless the context clearly dictates otherwise. Accordingly, unless the contrary is indicated, the numerical parameters set forth in this application are approximations that may vary depending upon the desired properties sought to be obtained by the present invention.

Unless otherwise indicated, some embodiments herein contemplate numerical ranges. When a numerical range is provided, unless otherwise indicated, the range includes the range endpoints. Unless otherwise indicated, numerical ranges include all values and subranges therein as if explicitly written out.

b. Overview

Disclosed herein are pharmaceuticals, compositions, kits, and methods for the prevention and/or treatment of hearing loss, for example, by administering a therapeutically effective amount of tetrandrine (TET) or a salt thereof. The TET or salt thereof can be administered in a therapeutically effective amount to protect the subject in need thereof from a hearing disorder, to restore hearing loss or to alleviate one or more symptoms of a hearing disorder, such as decreased speech recognition, tinnitus, vertigo or decreased memory.

c. Conditions to be Treated

Disclosed herein are pharmaceuticals, compositions, kits, and methods for the prevention and/or treatment of a hearing disorder, including, but not limited to, various conditions such as noise-induced hearing loss (NIHL), age-related hearing loss (ARHL or presbycusis), drug or injury-induced hearing loss, central auditory hearing disorder (CAPD), or tinnitus.

NIHL

NIHL is one of the most predominant health hazard posed by occupational and recreational settings. However, there are currently no FDA-approved drugs in diminishing NIHL and the development of an efficacious treatment has been hampered by the complex array of cellular and molecular pathways involved in NIHL. NIHL can cause damages range from exhaustion of the hair cells in the ear to loss of those cells. Therefore, NIHL can be the consequence of over-stimulation of the hair cells and supporting structures. Structural damage to hair cells (primarily the outer hair cells) can result in hearing loss that can be characterized by an attenuation and distortion of incoming auditory stimuli.

NIHL can be caused by a one-time exposure to excessive noise. For example, exposure to sound in excess of about 80 dB, 90 dB, 100 dB, 110 dB, 120 dB, 130 dB, 140 dB, or 150 dB in short periods can cause NIHL. Alternatively, NIHL can also be caused by repeated exposure to noise over a period of time. For example, exposure to sound in excess of about 60 dB, 65 dB, 70 dB, 75 dB, 80 dB, 85 dB, 90 dB, 95 dB, or 100 dB for more than 8 hours per day can cause NIHL. The symptoms of NIHL may include tinnitus, ear pain, hyperacusis, dizziness, vertigo and/or vestibular damages in the inner-ear.

Disclosed herein are pharmaceuticals, compositions, kits, and methods of treating or preventing hearing loss (e.g., NIHL) in a subject in need thereof wherein the methods comprise administering a therapeutically effective amount of TET or salt thereof. In some cases, the therapeutically effective amount of TET or salt thereof is an amount sufficient to reduce, or eliminate the NIHL. In some cases, the therapeutically effective amount of TET or salt thereof is an amount sufficient to halt or prevent the NIHL. In some cases, the therapeutically effective amount of TET or salt thereof is an amount sufficient to reverse the NIHL or at least partially restore hearing. The subject can be at risk of developing hearing loss (e.g., NIHL). Alternatively, the subject can be suffering hearing loss (e.g., NIHL).

ARHL or Presbycusis

ARHL or presbycusis is a major health problem for which there are currently no treatments or preventatives. Age-related hearing loss develops gradually over time and in its early stages may be practically imperceptible to the affected individual. The cause of an ARHL or presbycusis is generally considered to be degeneration of the auditory nervous system, especially the auditory nerves in the ears. It is the most common form of hearing loss in persons over 55 years of age.

Early noise injury can be a cause of ARHL or presbycusis. The subject can be suffering or at risk of developing hearing loss (e.g., ARHL or presbycusis). For example, the subject can be suffering or at risk of developing hearing loss (e.g., ARHL or presbycusis) at least at about 30 years, 35 years, 40 years, 45 years, 50 years, 55 years, 60 years, 65 years, 70 years, 75 years, 80 years, 85 years, 90 years, 95 years, or 100 years of age. In some cases, the subject can be about 50 years of age.

Disclosed herein are pharmaceuticals, compositions, kits, and methods of treating or preventing hearing loss (e.g., ARHL or presbycusis) in a subject in need thereof wherein the methods comprise administering a therapeutically effective amount of TET or salt thereof. In some cases, the therapeutically effective amount of TET or salt thereof is an amount sufficient to reduce, or eliminate the ARHL or presbycusis. In some cases, the therapeutically effective amount of TET or salt thereof is an amount sufficient to halt or prevent the ARHL or presbycusis. In some cases, the therapeutically effective amount of TET or salt thereof is an amount sufficient to reverse the ARHL or presbycusis or at least partially restore hearing. The subject can be at risk of developing hearing loss (e.g., ARHL or presbycusis). Alternatively, the subject can be suffering hearing loss (e.g., ARHL or presbycusis).

Injury or Drug-Induced Hearing Loss

Ototoxic drugs, such as chemotherapeutic agents, antineoplastic agents, antibiotics, loop-diuretics, quinines or a quinine-like compounds, and salicylate or salicylate-like compounds, can cause drug-induced hearing loss. For example, aminoglycosides are antibiotics that have been used for the treatment of Gram-negative bacterial infections and some aerobic Gram-positive bacterial infections. Despite their utility, however, they have serious side effects, including ototoxicity associated with the destruction of the sensory hair cells in organ of Corti of the cochlea of the inner ear. In addition, surgery near or on auditory nerve can cause hearing loss, which subsequently causes tinnitus.

Disclosed herein are pharmaceuticals, compositions, kits, and methods of treating or preventing hearing loss (e.g., injury or drug-induced hearing loss) in a subject in need thereof wherein the methods comprise administering a therapeutically effective amount of TET or salt thereof. In some cases, the therapeutically effective amount of TET or salt thereof is an amount sufficient to reduce, or eliminate this type of hearing loss. In some cases, the therapeutically effective amount of TET or salt thereof is an amount sufficient to halt or prevent this type of hearing loss. In some cases, the therapeutically effective amount of TET or salt thereof is an amount sufficient to not only prevent the drug-induced hearing loss or at least partially restore hearing. The subject can be at risk of developing hearing loss (e.g., drug-induced hearing loss). Alternatively, the subject can be suffering hearing loss (e.g., drug-induced hearing loss). In some cases, the therapeutically effective amount of TET or salt thereof is an amount sufficient to not only prevent the drug-induced hearing loss, but works synergistically with cancer drugs to kill cancer cells The therapeutically effective amount of TET or salt thereof can prevent onset of an injury- or drug-induced hearing loss. For example, disclosed herein are methods for preventing a drug-induced hearing loss, comprising administering a therapeutically effective amount of TET or salt thereof to a subject in need thereof prior to administering to the subject one or more ototoxic drugs for the treatment of a condition other than hearing loss. The administering a therapeutically effective amount of TET or salt thereof can begin up to about 12 months (e.g., 1 day to 60 days) prior to the administration of the one or more ototoxic drugs. The administering a therapeutically effective amount of TET or salt thereof can also begin on the same day as the administration of the one or more ototoxic drugs. In some cases, the administering a therapeutically effective amount of TET or salt thereof can begin up to about 12 months, e.g. 1 hour, 6 hours, 12 hours, 24 hours, 2 days, 4 days, 6 days, 8 days, 10 days, 20 days, 1 month, 2 months, 4 months, 6 months, 8 months, 10 months, or 12 months prior to the administration of the one or more ototoxic drugs. In some cases, the administering a therapeutically effective amount of TET or salt thereof can begin about 1 day to about 12 months, e.g. about 1 day to about 2 days, about 2 days to about 10 days, about 10 days to about 1 month, about 1 month to about 3 months, about 3 months to about 6 months, or about 6 months to about 12 months, prior to the administration of the one or more ototoxic drugs.

The therapeutically effective amount of TET or salt thereof can treat or prevent drug-induced hearing loss, such as amelioration of drug-induced hearing loss, reduction or elimination of tinnitus, partial or total rehabilitation of hearing, or prevention of further hearing loss arising out of ototoxic effects of the one or more ototoxic drugs. The methods disclosed herein provide for dosing of a pharmaceutical composition in response to a noted decrease in hearing function arising out of, or occurring during, dosing of one or more ototoxic drugs.

The administering a therapeutically effective amount of TET or salt thereof can be continued for the duration of the one or more ototoxic drugs. The administering a therapeutically effective amount of TET or salt thereof can stop on the same day as the cessation of the one or more ototoxic drugs. The administering a therapeutically effective amount of TET or salt thereof can continue for at least about 1 day, e.g. for at least about 1 day, 2 days, 4 days, 6 days, 8 days, 10 days, 20 days, 1 month, 2 months, 4 months, 6 months, 8 months, 10 months, or 12 months after cessation of the one or more ototoxic drugs. In some cases, the administering a therapeutically effective amount of TET or salt thereof can continue for about 1 day to about 12 months, e.g. about 1 day to about 2 days, about 2 days to about 10 days, about 10 days to about 1 month, about 1 month to about 3 months, about 3 months to about 6 months, or about 6 months to about 12 months after cessation of the one or more ototoxic drugs.

Some examples of ototoxic drugs include certain antibacterial and antineoplastic drugs. For example, some ototoxic drugs are chemotherapeutic agents, e.g. antineoplastic agents (e.g., a family of cisplatin based drugs or targeted cancer drugs such as Osimertinib), and antibiotics. Other possible candidates include loop-diuretics, quinines or a quinine-like compound, and salicylate or salicylate-like compounds. Thus, disclosed herein are pharmaceuticals, compositions, kits, and methods of treating or preventing hearing loss caused by an ototoxic drug, wherein the ototoxic drug can be an antineoplastic agent (e.g., ototoxic aminoglycoside antibiotic) such as cisplatin, an antibiotic such as an aminoglycoside, a loop-diuretic, a quinine, a quinine-like compound, a salicylate or salicylate-like compound.

Ototoxic aminoglycoside antibiotics include but are not limited to neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin, or combinations thereof. Particular antibiotics include neomycin B, kanamycin A, kanamycin B, gentamicin C1, gentamicin C1a, and gentamicin C2. Thus, disclosed herein are pharmaceuticals, compositions, kits, and methods of treating or preventing drug-induced hearing loss comprising administering to a subject, who has been, is being or will be treated with one or more aminoglycosides, a therapeutically effective amount of a pharmaceutical composition of the disclosure. In some cases, the ototoxic aminoglycoside antibiotic is not streptomycin. In some cases, the hearing disorder is not caused by ototoxic aminoglycoside antibiotics. In some cases, the hearing disorder is not caused by streptomycin.

Hearing impairments induced by aminoglycosides can be prevented or reduced by the pharmaceuticals, compositions, kits, and methods disclosed herein. Although the aminoglycosides are particularly useful due to their rapid bactericidal action against infections of aminoglycoside-susceptible organisms, their use has heretofore been limited to more severe, complicated infections because of ototoxic and nephrotoxic side-effects. For this reason the aminoglycosides have been considered to have a low therapeutic/risk ratio compared to other antibiotics used systemically. Thus, disclosed herein are also improved methods of treatment of aminoglycoside-susceptible infections, comprising administering to a subject an anti-bacterially effective amount of an aminoglycoside and a pharmaceutical composition disclosed herein. It is to be recognized that recommended doses of aminoglycosides have been established; and the methods disclosed herein are effective when administering aminoglycosides in a range of about 100 to about 500%, in particular about 100 to about 250%, and more particularly about 100 to about 150% of the currently recommended doses, which are available in general in the product labeling and package inserts for the commercially available drug aminoglycoside drug products. The improved methods provide prophylaxis against aminoglycoside-induced hearing loss and/or tinnitus, thereby expanding the therapeutic index of the aminoglycoside drug.

The disclosed pharmaceutical compositions can be co-administered with one or more ototoxic drugs in the same dosage form. For example, an improved method is provided for treatment of infection of a subject by administration of an aminoglycoside antibiotic and a therapeutically effective amount of a pharmaceutical composition disclosed herein. Alternatively, the aminoglycoside antibiotic and the pharmaceutical composition disclosed herein can be administered to the subject in separate dosage forms.

The one or more ototoxic drugs can also be chemotherapeutic drugs for treatment of cancer in a subject. For example, an improved method is provided for treatment of cancer in a subject by administration of a chemotherapeutic drug (e.g. cisplatin-based drugs or new targeted cancer drugs such as Osimertinib) and a therapeutically effective amount of a pharmaceutical composition disclosed herein.

Ototoxic antineoplastic chemotherapeutic agents include cisplatin or cisplatin-like compounds, taxol or taxol-like compounds, and other chemotherapeutic agents believed to cause ototoxin-induced hearing impairments, e.g., drugs targeted epidermal growth factor receptors (EGFRs) such as Osimertinib, or vincristine, an antineoplastic drug used to treat hematological malignancies and sarcomas. Thus, the methods disclosed herein can be used to treat ototoxicity (e.g. drug-induced hearing loss) in a subject, who will be, is being, or has been treated with an antineoplastic agent, including cisplatin or cisplatin-like compounds, taxol or taxol-like compounds, and other chemotherapeutic agents believed to cause ototoxin-induced hearing impairments, e.g., Osimertinib, or vincristine, an antineoplastic drug used to treat hematological malignancies and sarcomas.

Central Auditory Hearing Disorder (CAPD)

Central auditory processing disorders (CAPD) relate to difficulties in the perceptual processing of auditory information in the central nervous system (CNS). Tests for CAPD can include: auditory discrimination tests; auditory temporal processing and patterning tests; dichotic speech tests; monaural low-redundancy speech tests; binaural interaction tests; electroacoustic measures; and electrophysiological measures.

Disclosed herein are pharmaceuticals, compositions, kits, and methods of treating or preventing hearing loss (e.g., CAPD) in a subject in need thereof wherein the methods comprise administering a therapeutically effective amount of TET or salt thereof. In some cases, the therapeutically effective amount of TET or salt thereof is an amount sufficient to reduce, or eliminate the CAPD. In some cases, the therapeutically effective amount of TET or salt thereof is an amount sufficient to halt or prevent the CAPD. In some cases, the therapeutically effective amount of TET or salt thereof is an amount sufficient to reverse the CAPD or at least partially restore hearing. The subject can be at risk of developing hearing loss (e.g., CAPD). Alternatively, the subject can be suffering hearing loss (e.g., CAPD).

Tinnitus

Tinnitus is the perception of sound in the ears even without external auditory stimulation. The most frequent manifestation of tinnitus is a ringing in the ears; however, tinnitus can also present as crickets, whooshing, pulsing, ocean waves, buzzing, even music, Tinnitus can be temporary, intermittent or even permanent; and its severity can range from a quiet background ringing to an overwhelming auditory sensation that drowns out external sources of sound Tinnitus can be caused by one or more factors, such as administration of, or exposure to, ototoxic substances (such as an aspirin overdose), exposure to a short burst of extreme noise (e.g. gunshot or explosion) or prolonged exposure to high decibel noise (such as aircraft engine noise, high decibel music concerts or high decibel headphone usage), or central auditory processing disorders as discussed herein.

Disclosed herein are pharmaceuticals, compositions, kits, and methods of treating or preventing hearing disorder (e.g., tinnitus) in a subject in need thereof wherein the methods comprise administering a therapeutically effective amount of TET or salt thereof. In some cases, the therapeutically effective amount of TET or salt thereof is an amount sufficient to reduce, or eliminate the hearing disorder (e.g., tinnitus). In some cases, the therapeutically effective amount of TET or salt thereof is an amount sufficient to halt or prevent the hearing disorder (e.g., tinnitus). In some cases, the therapeutically effective amount of TET or salt thereof is an amount sufficient to reverse the hearing disorder (e.g., tinnitus) or at least partially restore hearing. The subject can be at risk of developing the hearing disorder (e.g., tinnitus). Alternatively, the subject can be suffering the hearing disorder (e.g., tinnitus).

d. Effective Dosage Ranges

The therapeutically effective amount of TET or salt thereof can be dependent on the weight of a subject. In some cases, the therapeutically effective amount of TET or salt thereof is at least about 1 µg of TET or salt thereof per kg of the subject, for example at least about 1, 2, 3, 4, 5, 6, 7, 8, 9, 10, 20, 30, 40, 50, 60, 70, 80, 90, 100, 200, 300, 400, 500, 600, 700, 800, 900, or 1000 µg of TET or salt thereof per kg of the subject. In some cases, the therapeutically effective amount of TET or salt thereof is at least about 1 mg of TET or salt thereof per kg of the subject, for example at least about 1, 2, 3, 4, 5, 6, 7, 8, 9, 10, 20, 30, 40, 50, 60, 70, 80, 90, 100, 200, 300, 400, 500, 600, 700, 800, 900, or 1000 mg of TET or salt thereof per kg of the subject. In some cases, the therapeutically effective amount of TET or salt thereof is less than about 1000 µg of TET or salt thereof per kg of the subject, for example less than about 1, 2, 3, 4, 5, 6, 7, 8, 9, 10, 20, 30, 40, 50, 60, 70, 80, 90, 100, 200, 300, 400, 500, 600, 700, 800, 900 or 1000 µg of TET or salt thereof per kg of the subject. In some cases, the therapeutically effective amount of TET or salt thereof is less than about 1000 mg of TET or salt thereof per kg of the subject, for example less than about 1, 2, 3, 4, 5, 6, 7, 8, 9, 10, 20, 30, 40, 50, 60, 70, 80, 90, 100, 200, 300, 400, 500, 600, 700, 800, 900 or 1000 mg of TET or salt thereof per kg of the subject. In some cases, the therapeutically effective amount of TET or salt thereof ranges from about 1 µg to 1000 µg of TET or salt thereof per kg of the subject, for example about 1-700, 1-500, 1-300, 1-100, 1-50, 1-10, 10-700, 10-500, 10-300, 10-100, 10-80, 10-60, 10-40, 10-20, 50-700, 50-500, 50-300, 50-100, 100-700, 100-500, 100-300, 300-700, 300-500, or 500-700 µg of TET or salt thereof per kg of the subject. In some cases, the therapeutically effective amount of TET or salt thereof ranges from about 1 µg to about 10 µg of TET or salt thereof per kg of the subject. In some cases, the therapeutically effective amount of TET or salt thereof ranges from about 10 µg to about 100 µg of TET or salt thereof per kg of the subject. In some cases, the therapeutically effective amount of TET or salt thereof ranges from about 100 µg to about 500 µg of TET or salt thereof per kg of the subject. In some cases, the therapeutically effective amount of TET or salt thereof ranges from about 1 µg to about 1000 mg of TET or salt thereof per kg of the subject, for example about 1-700, 1-500, 1-300, 1-100, 1-50, 1-10, 10-700, 10-500, 10-300, 10-100, 10-80, 10-60, 10-40, 10-20, 50-700, 50-500, 50-300, 50-100, 100-700, 100-500, 100-300, 300-700, 300-500, or 500-700 mg of TET or salt thereof per kg of the subject. In some cases, the therapeutically effective amount of TET or salt thereof ranges from about 16 mg to about 24 mg of TET or salt thereof per kg of the subject. In some cases, the therapeutically effective amount of TET or salt thereof ranges from about 30 mg to about 100 mg of TET or salt thereof per kg of the subject. In some cases, the therapeutically effective amount of TET or salt thereof ranges from about 50 mg to about 140 mg of TET or salt thereof per kg of the subject. In some cases, the therapeutically effective amount of TET or salt thereof ranges from about 115 mg to about 125 mg of TET or salt thereof per kg of the subject. The therapeutically effective amount of TET or salt thereof can also be the daily dosage of TET or salt thereof for the subject.

In pharmaceutical compositions with the therapeutically effective amount of TET or salt thereof and one or more API, the amount of API in the pharmaceutical composition can be dependent on the weight of a subject. In some cases, the amount of API in the pharmaceutical composition is at least about 1 mg of API per kg of the subject, for example at least about 1, 2, 3, 4, 5, 6, 7, 8, 9, 10, 20, 30, 40, 50, 60, 70, 80, 90, 100, 200, 300, 400, 500, 600, 700, 800, 900 or 1000 mg of API per kg of the subject. In some cases, the amount of API in the pharmaceutical composition is less than about 1 mg of API per kg of the subject, for example less than about 1, 2, 3, 4, 5, 6, 7, 8, 9, 10, 20, 30, 40, 50, 60, 70, 80, 90, 100, 200, 300, 400, 500, 600, 700, 800, 900 or 1000 mg of API per kg of the subject. In some cases, the amount of API in the pharmaceutical composition ranges from about 1-1000 mg of API per kg of the subject, for example about 1-700, 1-500, 1-300, 1-100, 1-50, 1-10, 10-700, 10-500, 10-300, 10-100, 10-80, 10-60, 10-40, 10-20, 50-700, 50-500, 50-300, 50-100, 100-700, 100-500, 100-300, 300-700, 300-500, or 500-700 mg of API per kg of the subject. In some cases, the therapeutically effective amount of API ranges from about 16 mg to about 24 mg of API per kg of the subject. In some cases, the therapeutically effective amount of API ranges from about 30 mg to about 100 mg of API per kg of the subject. In some cases, the therapeutically effective amount of API ranges from about 50 mg to about 140 mg of API kg of the subject. The therapeutically effective amount of API can also be the daily dosage of API for the subject. For instance, the daily dosage of the antioxidants, NMDA antagonists, SSRI or combined SSRI/NMDA antagonists can be about 1 to about 500 mg/day, preferably about 4 to about 250 mg/day.

The concentration of TET or salt thereof in pharmaceutical compositions can be at least about 0.1%, e.g. at least about 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, or 90% by weight. The concentration of TET or salt thereof in pharmaceutical compositions can be less than about 99%, e.g. less than about 10%, 15%, 20%, 25%, 30%, 35%, 40%, 45%, 50%, 55%, 60%, 65%, 70%, 75%, 80%, 85%, 90% or 99% by weight. The concentration of TET or salt thereof in pharmaceutical compositions can range from about 0.1 to 99%, e.g. 0.1 to 0.5%, 0.1 to 1%, 0.5 to 1%, 1 to 2%, 1 to 5%, 1 to 10%, 2 to 5%, 2 to 10%, 5 to 10%, 10 to 15%, 15 to 20%, 20 to 30%, 30 to 50%, 50 to 70%, 70 to 90%, 90 to 95%, or 95 to 99% by weight. In some cases, the concentrations of TET or salt thereof in pharmaceutical compositions range from about 1% to about 10%. In some cases, the concentrations of TET or salt thereof in pharmaceutical compositions range from about 10% to about 50%. In some cases, the concentrations of TET or salt thereof in pharmaceutical compositions range from about 70 to about 90%.

The concentration of API in pharmaceutical compositions can be at least about 0.1%, e.g. at least about 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, or 90% by weight. The concentration of API in pharmaceutical compositions can be less than about 99%, e.g. less than about 10%, 15%, 20%, 25%, 30%, 35%, 40%, 45%, 50%, 55%, 60%, 65%, 70%, 75%, 80%, 85%, 90% or 99% by weight. The concentration of API in pharmaceutical compositions can range from about 0.1% to about 99%, e.g. 0.1 to 0.5%, 0.1 to 1%, 0.5 to 1%, 1 to 2%, 1 to 5%, 1 to 10%, 2 to 5%, 2 to 10%, 5 to 10%, 10 to 15%, 15 to 20%, 20 to 30%, 30 to 50%, 50 to 70%, 70 to 90%, 90 to 95%, or 95 to 99% by weight. In some cases, the concentrations of API in pharmaceutical compositions range from about 1% to about 10%. In some cases, the concentrations of API in pharmaceutical compositions range from about 10% to about 50%. In some cases, the concentrations of API in pharmaceutical compositions range from about 70% to about 90%.

The therapeutically effective amount of TET or salt thereof can be in a tablet, capsule, caplet, gel cap, powder, or solution dosage form. The tablet, capsule, caplet, gel cap, powder, or solution dosage form can have a unit weight of at least about 1 mg, e.g. at least about 1, 2, 3, 4, 5, 6, 7, 8, 9, 10, 20, 30, 40, 50, 60, 70, 80, 90, 100, 200, 300, 400, 500, 600, 700, 800, or 900 mg. The tablet, capsule, caplet, gel cap, powder, or solution dosage form can have a unit weight of at least about 1 g, e.g. at least about 1, 2, 3, 4, 5, 6, 7, 8, 9, 10, 20, 30, 40, 50, 60, 70, 80, 90, or 100 g. The tablet, capsule, caplet, gel cap, powder, or solution dosage form can have a unit weight of less than about 1000 mg, e.g. at least about 1, 2, 3, 4, 5, 6, 7, 8, 9, 10, 20, 30, 40, 50, 60, 70, 80, 90, 100, 200, 300, 400, 500, 600, 700, 800, or 900 mg. The tablet, capsule, caplet, gel cap, powder, or solution dosage form can have a unit weight of less than about 100 g, e.g. less than about 1, 2, 3, 4, 5, 6, 7, 8, 9, 10, 20, 30, 40, 50, 60, 70, 80, 90, or 100 g. The tablet, capsule, caplet, gel cap, powder, or solution dosage form can have a unit weight of ranges from about 1 mg to 10 g, e.g. ranges about 1 mg to about 10 mg, about 10 mg to about 50 mg, about 50 mg to about 100 mg, about 100 mg to about 200 mg, about 200 mg to about 400 mg, about 400 mg to about 600 mg, about 600 mg to about 800 mg, about 800 mg to about 1 g, about 1 g to about 2 g, about 2 g to about 5 g, or about 5 g to about 10 g. The therapeutically effective amount of TET or salt thereof can be in a solution dosage form. The solution dosage form can have a unit volume of at least about 1 mL, e.g. at least about 1, 2, 3, 4, 5, 6, 7, 8, 9, 10, 20, 30, 40, 50, 60, 70, 80, 90, 100, 200, 300, 400, 500, 600, 700, 800, or 900 mL. The solution dosage form can have a unit volume of less than about 1000 mL, e.g. less than about 1, 2, 3, 4, 5, 6, 7, 8, 9, 10, 20, 30, 40, 50, 60, 70, 80, 90, 100, 200, 300, 400, 500, 600, 700, 800, or 900 mL. The solution dosage form can have a unit volume ranges from about 1 to about 500 mL, e.g. ranges about 1-500, 1-300, 1-100, 1-80, 1-60, 1-40, 1-20, 1-10, 1-5, 10-500, 10-300, 10-100, 10-80, 10-60, 10-40, 10-20, 20-500, 20-300, 20-100, 20-80, 20-60, 20-40, 40-500, 40-300, 40-100, 40-80, 40-60, 60-500, 60-300, 60-100, 60-80, 80-500, 80-300, 80-100, 100-500, 100-300, or 300-500 mL.

e. Pathways

Disclosed herein are pharmaceuticals, compositions, kits, and methods of preventing or treating a hearing disorder by administering TET or salt thereof, for example, a therapeutically effective amount of TET or salt thereof. In some cases, the administering TET or salt thereof can comprise administering a product (e.g., nutraceutical product) comprising TET or salt thereof. In some cases, the product comprises one or more compositions extracted from an herb containing TET or salt thereof. In some cases, the herb is *Stephania tetrandra* (e.g., *Stephania tetrandra* S. Moor).

TET is a bis-benzylisoquinoline alkaloidsoxazole derivative ($C_{38}H_{42}O_6N_2$), originally extracted from *Stephania tetrandra* of the Menispermaceae family. The PK study in rats showed that the TET drug concentration-curve fits well with a two-compartment open model, and the drug elimination from plasma is consistent with linear kinetics between 12.5 to 25 mg/kg. With a single oral TET administration (50 mg/kg) in rats, the area under the curve (AUC) is 6279.2+/−2411.5 (μg h/L), maximal plasma concentration (Cmax) is 237.1+/−95.9 (μg h/L), and half time (T½) is 20.6+/−3.7 (h). At higher dosages, limited side effects can be observed in patients including abdominal distension, diarrhea, dry eye, itching, hyperpigmentation, and mildly elevated liver enzymes. All these symptoms can resolve spontaneously after discontinuance of the medication.

TET's calcium channel antagonism can provide protection against noise-induced loss and damage of hair cells within the cochlea of the inner ear. TET's sodium channel blocking activity can reduce transmission of the abnormal sounds and auditory sensations associated with tinnitus. TET's carbonic anhydrase inhibitory activity can help to reduce fluid accumulation associated with trauma and other disorders of the inner ear. TET's ability to stimulate central nervous system serotonin neurotransmission can also facilitate central auditory processing of sounds and speech.

Multiple pathways can be regulated in treating and/or preventing hearing loss by administrating TET or salt thereof, e.g. a therapeutically effective amount of TET or salt thereof. For example, methods for regulating oxidative pathway in a subject in need thereof can comprise administering a therapeutically effective amount of TET or salt thereof. The oxidative pathway can be regulated by decreasing oxidative stress, down-regulating miRNA-155, decreasing TNF-α in the NF-κB signaling pathway, or a combination thereof. The oxidative pathway can be regulated by scavenging free radicals. The oxidative pathway can be regulated by lowering peroxide levels. The oxidative pathway can be regulated by regulating cellular redox states. The oxidative pathway can be regulated by inhibiting reactive oxygen species formation, suppressing up-regulation of Mac-1, neutrophil adhesion to fibrinogen, or any combination thereof. The oxidative pathway can be regulated by preventing hydrogen peroxide-induced oxidative neuronal cell damage.

Methods for regulating calcium signaling pathways in a subject in need thereof can comprise administering a therapeutically effective amount of TET or salt thereof. The calcium signaling pathways can be regulated by inhibiting calcium influx via voltage-activated calcium channel, α2-adrenoceptor-operated calcium channel, or both. The calcium signaling pathways can be regulated by inhibiting cytosolic calcium pool release, for example, in corpus cavernosum smooth muscle cells. The calcium signaling pathways can be regulated by inhibiting tumor necrosis factor-alpha production, for example, induced by calcium entry. The calcium signaling pathways can be regulated by blocking the voltage-gated calcium channels. The calcium signaling pathways can be regulated by affecting the function of calcium-ATPase, calcium release channels, or both.

The calcium signaling pathways can be regulated by releasing intracellular calcium, blocking calcium entry, or both. The calcium signaling pathways can be regulated by blocking endosomal calcium channels, e.g. two-pore channel. The calcium signaling pathways can be regulated by blocking T-type and/or L-type calcium current. The calcium signaling pathways can be regulated by inhibiting activity of BKCa channels. The calcium signaling pathways can be regulated by inhibiting calcium-release activated channels.

Methods for regulating anti-inflammation pathways in a subject in need thereof can comprise administering a therapeutically effective amount of TET or salt thereof. The anti-inflammation pathways can be regulated by reducing tube formation in angiogenic process. For example, the reducing tube formation in angiogenic process can inhibit on post-receptor pathway of IL-1a and/or platelet-derived growth factor-BB in chronic inflammation. The anti-inflammation pathways can be regulated by suppressing leukocyte infiltration into air pouches induced by IL-1 and/or TNF. The anti-inflammation pathways can be regulated by inhibiting prostaglandin E synthesis. The anti-inflammation pathways can be regulated by inhibiting IL-1, TNF-α IL-6, IL-8, IgG, phagocytosis by neutrophils, or any combination thereof. For example, the IL-1, TNF-α IL-6, and/or IL-8 can be from monocytes. The IgG can be from B cells. The anti-inflammation pathways can be regulated by suppressing lipopolysaccharide-induced increase of TNF-α, IL-1β, and/or high mobility group box 1 secretion by peritoneal macrophages.

Methods for regulating central monoaminergic neurotransmitter system in a subject in need thereof can also comprise administering a therapeutically effective amount of TET or salt thereof. Methods for regulating levels of brain-derived neurotrophic factor (BDNF) in a subject in need thereof can comprise administering a therapeutically effective amount of TET or salt thereof. Methods for inhibiting function of acetylcholine nicotinic receptors in a subject in need thereof can comprise administering a therapeutically effective amount of TET or salt thereof.

The subject can refer to human or non-human animals. In some cases, the subject can refer to human, including those in need of treatment thereof. In other cases, the subject can refer to non-human animals, such as a pig, a cat, a cattle, a deer, a dog, a ferret, a gaur, a goat, a horse, a mouse, a mouflon, a mule, a rabbit, a rat, or a sheep, or a primate (e.g., a monkey, or a chimpanzee). In some cases, the subject is at risk of developing hearing loss. In some cases, the subject has developed hearing loss.

f. Combination Treatment

The therapeutically effective amount of TET or salt thereof can be the sole active pharmaceutical ingredients (API). Alternatively, the therapeutically effective amount of TET or salt thereof can be used in combination with one or more additional API. Disclosed herein are pharmaceuticals, compositions, kits, and methods of preventing or treating a hearing disorder by administering TET or salt thereof, e.g. therapeutically effective amount of TET or salt thereof, and one or more active pharmaceutical ingredients (API), e.g. therapeutically effective amount of API.

The one or more API can comprise one or more antioxidants, spin-trapping agents, N-methyl-D-aspartate (NMDA) antagonists, selective serotonin reuptake inhibitors (SSRI), dopamine releasing agents (DRA), acetylcholine release inducers, norepinephrine reuptake inhibitors (NERI), monoamineoxidase-A inhibitors (MAI), serotonin reuptake inhibitors (SRI), serotonin-norepinephrine reuptake inhibitors (SNRI), calcium channel blockers (CCB), norepinephrine selective reuptake inhibitors (NSRI), 5HT serotonin reuptake inhibitors (5HT SRI), zonisamide, gabapentin, cannabinoid, or any combinations thereof.

TET & Antioxidants and/or Spin-Trapping Agents

Disclosed herein are pharmaceuticals, compositions, kits, and methods of preventing or treating a hearing disorder by administering TET or salt thereof, e.g. therapeutically effective amount of TET or salt thereof, and one or more antioxidants and/or one or more spin-trapping agent.

The pharmaceuticals, compositions, kits, and methods can protect against noise-induced hearing loss, reduce transmission of abnormal sounds and auditory sensations associated with tinnitus, reduce fluid accumulation in the inner ear, facilitate central auditory processing of sounds and speech, or combinations thereof, comprising administering TET or salt thereof and one or more API that bind to or metabolize reactive oxygen species and provide protection against the damage induced by oxygen species, which are toxic mediators. In some such cases, TET or salt thereof is administered in combination with an antioxidant or spin trapping agent. In some such cases, TET or salt thereof is administered in combination with allopurinol, methionine or L-carnitine. In particular cases, TET or salt thereof is administered in combination with allopurinol. In other particular cases, TET or salt thereof is administered in combination with glutathione. In still further particular cases, TET or salt thereof is administered in combination with methionine. In yet further cases, TET or salt thereof is administered in combination with L-carnitine. In yet further cases, TET or salt thereof is administered in combination with two or more antioxidants, such as allopurinol, glutathione, methionine, or L-carnitine. In still further cases, TET or salt thereof is administered in combination with one or more antioxidants, such as allopurinol, glutathione, methionine, or L-carnitine, and one or more other active pharmaceutical ingredients, such as one or more NMDA antagonists, one or more SSRIs or one or more compounds having both SSRI and NMDA antagonist activity, such as alaproclate (2-(p-chlorophenyl)-1,1-dimethyl 2-aminopropanoate).

In some cases, TET or salt thereof is administered in the same dosage form as one or more antioxidants or spin trapping agents. In some such cases, the TET or salt thereof is mixed with one or more antioxidants or spin trapping agents. In other cases, the TET or salt thereof is segregate from the antioxidant or spin trapping agent by a coating, a shell, a capsule or some other means for preventing admixture of TET or salt thereof with the antioxidant or spin trapping agent, while maintaining both ingredients in the same dosage form.

TET & NMDA Antagonists

Disclosed herein are pharmaceuticals, compositions, kits, and methods of preventing or treating a hearing disorder by administering TET or salt thereof, e.g. therapeutically effective amount of TET or salt thereof, and one or more NMDA antagonists. The pharmaceuticals, compositions, kits, and methods can protect against noise-induced hearing loss, reduce transmission of abnormal sounds and auditory sensations associated with tinnitus, reduce fluid accumulation in the inner ear, facilitate central auditory processing of sounds and speech, or combinations thereof, comprising administering TET or salt thereof and one or more API that block the excitotoxic actions of glutamate within the inner ear. Glutamate is a mediator of noise-induced damage to the hair cells of the inner ear and blocking N-methyl-D-aspartate (NMDA) receptors provides protection against the toxic effects of glutamate. In some cases, TET or salt thereof is administered in a single dosage form comprising TET or salt thereof and a NMDA antagonist.

In some such cases, TET or salt thereof is administered in a single dosage form comprising an antagonist of N-methyl-D-aspartate, such as magnesium, riluzole, caroverine, memantine or a combination of two or more thereof. In particular cases, TET or salt thereof is administered in a single dosage form comprising riluzole. In other particular cases, TET or salt thereof is administered in a single dosage form comprising caroverine. In still further particular cases, TET or salt thereof is administered in a single dosage form comprising memantine. In still further particular cases, TET or salt thereof is administered in a single dosage form comprising magnesium. In yet further cases, TET or salt thereof is administered in a dosage form comprising two or more NMDA antagonists, such as magnesium, riluzole, caroverine, or memantine. In still further cases, TET or salt thereof is administered in a single dosage form comprising one or more NMDA antagonists, such as magnesium, riluzole, caroverine, or memantine, and one or more other active pharmaceutical ingredients, such as one or more antioxidants or spin trapping agents, one or more SSRIs or one or more compounds having both SSRI and NMDA antagonist activity.

In some such cases, TET or salt thereof is administered in a dosage form separate from that containing an NMDA antagonist, such as magnesium, riluzole, caroverine, memantine or a combination of two or more thereof. In particular cases, TET or salt thereof is administered in one dose and magnesium is administered in a separate dose. In particular cases, TET or salt thereof is administered in one dose and riluzole is administered in a separate dose. In other particular cases, TET or salt thereof is administered in one dose and caroverine is administered in a separate dose. In still further particular cases, TET or salt thereof is administered in one dose and memantine is administered in another dose. In yet further cases, TET or salt thereof is administered in one dose and two or more NMDA antagonists, such as magnesium, riluzole, caroverine, or memantine are administered in a separate dose. In still further cases, TET or salt thereof is administered one dose and one or more NMDA antagonists, such as magnesium, riluzole, caroverine, or memantine, and one or more other active pharmaceutical ingredients, such as one or more antioxidants or spin trapping agents, one or more SSRIs or one or more compounds having both SSRI and NMDA antagonist activity, are administered in a separate dose.

As mentioned above, in some cases, TET or salt thereof is administered in the same dosage form as one or more NMDA antagonists. In some such cases, the TET or salt thereof is mixed directly with one or more NMDA antagonists. In other cases, the TET or salt thereof is segregate from one or more NMDA antagonists by a coating, a shell, a capsule or some other means for preventing admixture of TET or salt thereof with the antioxidant or spin trapping agent, while maintaining both ingredients in the same dosage form.

TET & SSRI

Disclosed herein are pharmaceuticals, compositions, kits, and methods of preventing or treating a hearing disorder by administering TET or salt thereof, e.g. therapeutically effective amount of TET or salt thereof, and one or more SSRI. The pharmaceuticals, compositions, kits, and methods can protect against noise-induced hearing loss, reduce transmission of abnormal sounds and auditory sensations associated with tinnitus, reduce fluid accumulation in the inner ear, facilitate central auditory processing of sounds and speech, or combinations thereof, comprising administering TET or salt thereof and one or more API that enhance synaptic levels of serotonin in the brain and enhance hearing by improving auditory processing, increasing the signal: noise ratio of environmental sounds, and/or by heightening attention.

In some such cases, TET or salt thereof is administered in combination with a selective serotonin reuptake inhibitor (SSRI). In some such cases, TET or salt thereof is administered in combination with fluoxetine, sertraline, S-citalopram or combinations thereof. In particular cases, TET or salt thereof is administered in combination with fluoxetine. In other particular cases, TET or salt thereof is administered in combination with sertraline. In still further particular cases, TET or salt thereof is administered in combination with S-citalopram. In still further cases, TET or salt thereof is administered in combination with two or more SSRI agents, such as fluoxetine, sertraline or S-citalopram.

In some advantageous cases, TET or salt thereof is administered in combination with at least one SSRI and at least one NMDA antagonist. In exemplary cases, TET or salt thereof is administered in combination with at least one SSRI (such as fluoxetine, sertraline, S-citalopram or combinations of two or more thereof) and one or more NMDA antagonists selected from magnesium, riluzole, caroverine and memantine. In some particular cases, TET or salt thereof is administered in combination with at least one SSRI (such as fluoxetine, sertraline, S-citalopram or combinations of two or more thereof) and magnesium. In some particular cases, TET or salt thereof is administered in combination with at least one SSRI (such as fluoxetine, sertraline, S-citalopram or combinations of two or more thereof) and riluzole. In other particular cases, TET or salt thereof is administered in combination with at least one SSRI (such as fluoxetine, sertraline, S-citalopram or combinations of two or more thereof) and caroverine. In yet other cases, TET or salt thereof is administered in combination with at least one SSRI (such as fluoxetine, sertraline, S-citalopram or combinations of two or more thereof) and memantine. In yet further cases, TET or salt thereof is administered in combination with at least one SSRI (such as fluoxetine, sertraline, S-citalopram or combinations of two or more thereof) and a combination of two or more of magnesium, riluzole, caroverine and memantine.

In some cases, TET or salt thereof is administered in a combination comprising at least one at least one agent having combined SSRI and NMDA antagonist activity.

In some cases, TET or salt thereof is administered in a dosage form comprising at least one agent having both SSRI and NMDA antagonist activity or at least one SSRI and at least one NMDA antagonist. In some such cases, the dosage form further comprises at least one antioxidant or spin trapping agent.

In some cases, TET or salt thereof is administered in a dosage form separate from at least one agent having both SSRI and NMDA antagonist activity or TET or salt thereof is administered in a dosage form separate from at least one SSRI or at least one NMDA antagonist. In some such cases, the TET or salt thereof is mixed with one or more at least one agent having both SSRI and NMDA antagonist activity or TET or salt thereof is mixed with at least one SSRI or at least one NMDA antagonist. In other cases, the TET or salt thereof is segregate from the SSRI/NMDA antagonist, SSRI or NMDA antagonist by a coating, a shell, a capsule or some other means for preventing admixture of TET or salt thereof and the other active pharmaceutical ingredient, while maintaining the ingredients in the same dosage form.

TET & Dopamine Releasing Agent (DRA)

Disclosed herein are pharmaceuticals, compositions, kits, and methods of preventing or treating a hearing disorder by administering TET or salt thereof, e.g. therapeutically effective amount of TET or salt thereof, and one or more DRA. The pharmaceuticals, compositions, kits, and methods can protect against noise-induced hearing loss, reduce transmission of abnormal sounds and auditory sensations associated with tinnitus, reduce fluid accumulation in the inner ear, facilitate central auditory processing of sounds and speech, or combinations thereof, comprising administering TET or salt thereof and one or more DRA, such as amantadine. Amantadine can be a dopamine releasing agent and a N-methyl-D-aspartate antagonist. The dopamine releasing effect of amantadine can enhance auditory processing, while the NMDA antagonistic effect can protect inner ear hair cells from glutamate-induced toxicity.

In some cases, amantadine and TET or salt thereof are combined in the same dosage form. In particular cases, amantadine and TET or salt thereof are mixed together. In other cases, amantadine and TET or salt thereof are combined with one or more excipients to form a biphasic dosage form, wherein amantadine and TET or salt thereof occupy separate phases.

In other cases, amantadine and TET or salt thereof are administered in separate dosage forms. In particular cases, the separate dosage forms are administered simultaneously or substantially simultaneously (e.g. within about 10 minutes of one another, more particularly within about 5 minutes of one another, even more particularly within about 2 minutes of one another). In other cases, the separate dosage forms are administered at substantially different times (e.g. more than about 10 minutes apart, more particularly more than about an hour apart). The dosage forms can include those that are currently or presently commercially available, as well as those available to the person having skill in the art. They can include tablets, capsules, caplets, gel caps, powders, solutions, etc.

In some cases, the separate dosage forms of amantadine and TET or salt thereof are provided in a kit, such as is defined in more detail below. In specific cases, the separate dosages are provided in a kit including instructions for the administration of amantadine and TET or salt thereof for the prevention or treatment of a hearing disorder, especially for the prevention or treatment of hearing loss, tinnitus or both.

TET & Acetylcholine Release Inducers/NERI

Disclosed herein are pharmaceuticals, compositions, kits, and methods of preventing or treating a hearing disorder by administering TET or salt thereof, e.g. therapeutically effective amount of TET or salt thereof, and one or more acetylcholine release inducers and/or NERI. The pharmaceuticals, compositions, kits, and methods can protect against noise-induced hearing loss, reduce transmission of abnormal sounds and auditory sensations associated with tinnitus, reduce fluid accumulation in the inner ear, facilitate central auditory processing of sounds and speech, or combinations thereof, comprising administering TET or salt thereof and one or more acetylcholine release inducers and/or NERI, such as bifemelane. Bifemelane can be an acetylcholine release inducer, an antioxidant, a N-methyl-D-aspartate antagonist and/or a norepinephrine reuptake inhibitor. The ability of bifemelane to enhance brain levels of acetylcholine and norepinephrine can improve auditory processing, speech recognition and hearing perception. The ability of bifemelane to block N-methyl-D-aspartate receptors and to act as an antioxidant can provide protection to the inner ear cells.

In some cases, acetylcholine release inducers/NERI (e.g. amantadine) and TET or salt thereof are combined in the same dosage form. In particular cases, acetylcholine release inducers/NERI (e.g. amantadine) and TET or salt thereof are mixed together. In other cases, acetylcholine release inducers/NERI (e.g. amantadine) and TET or salt thereof are combined with one or more excipients to form a biphasic dosage form, wherein acetylcholine release inducers/NERI (e.g. amantadine) and TET or salt thereof occupy separate phases.

In other cases, acetylcholine release inducers/NERI (e.g. amantadine) and TET or salt thereof are administered in separate dosage forms. In particular cases, the separate dosage forms are administered simultaneously or substantially simultaneously (e.g. within about 10 minutes of one another, more particularly within about 5 minutes of one another, even more particularly within about 2 minutes of one another). In other cases, the separate dosage forms are administered at substantially different times (e.g. more than about 10 minutes apart, more particularly more than about an hour apart). The dosage forms can include those that are currently or presently commercially available, as well as those available to the person having skill in the art. They can include tablets, capsules, caplets, gel caps, powders, solutions, etc.

In some cases, the separate dosage forms of acetylcholine release inducers/NERI (e.g. amantadine) and TET or salt thereof are provided in a kit, such as is defined in more detail below. In specific cases, the separate dosages are provided in a kit including instructions for the administration of acetylcholine release inducers/NERI (e.g. amantadine) and TET or salt thereof for the prevention or treatment of a hearing disorder, especially for the prevention or treatment of hearing loss, tinnitus or both.

TET & Monoamineoxidase-A Inhibitors (MAI) and/or Serotonin Reuptake Inhibitors (SRI)

Disclosed herein are pharmaceuticals, compositions, kits, and methods of preventing or treating a hearing disorder by administering TET or salt thereof, e.g. therapeutically effective amount of TET or salt thereof, and one or more MAI and/or SRI. The pharmaceuticals, compositions, kits, and methods can protect against noise-induced hearing loss, reduce transmission of abnormal sounds and auditory sensations associated with tinnitus, reduce fluid accumulation in the inner ear, facilitate central auditory processing of sounds and speech, or combinations thereof, comprising administering TET or salt thereof and one or more MAI and/or SRI, such as pirlindole. Pirlindole can be a monoamineoxidase-A inhibitor, a serotonin reuptake inhibitor and an antioxidant. Pirlindole can increase norepinephrine and serotonin enhance auditory processing. The antioxidant activity of pirlindole can provide protection to inner ear hair cells from damage caused by reactive oxidative species.

In some cases, MAI and/or SRI (e.g. pirlindole) and TET or salt thereof are combined in the same dosage form. In particular cases, MAI and/or SRI (e.g. pirlindole) and TET or salt thereof are mixed together. In other cases, MAI and/or SRI (e.g. pirlindole) and TET or salt thereof are combined with one or more excipients to form a biphasic dosage form, wherein MAI and/or SRI (e.g. pirlindole) and TET or salt thereof occupy separate phases.

In other cases, MAI and/or SRI (e.g. pirlindole) and TET or salt thereof are administered in separate dosage forms. In particular cases, the separate dosage forms are administered simultaneously or substantially simultaneously (e.g. within about 10 minutes of one another, more particularly within about 5 minutes of one another, even more particularly within about 2 minutes of one another). In other cases, the separate dosage forms are administered at substantially different times (e.g. more than about 10 minutes apart, more particularly more than about an hour apart). The dosage forms can include those that are currently or presently commercially available, as well as those available to the person having skill in the art. They can include tablets, capsules, caplets, gel caps, powders, solutions, etc.

In some cases, the separate dosage forms of MAI and/or SRI (e.g. pirlindole) and TET or salt thereof are provided in a kit, such as is defined in more detail below. In specific cases, the separate dosages are provided in a kit including instructions for the administration of MAI and/or SRI (e.g. pirlindole) and TET or salt thereof for the prevention or treatment of a hearing disorder, especially for the prevention or treatment of hearing loss, tinnitus or both.

TET & Serotonin-Norepinephrine Reuptake Inhibitors (SNRI)

Disclosed herein are pharmaceuticals, compositions, kits, and methods of preventing or treating a hearing disorder by administering TET or salt thereof, e.g. therapeutically effective amount of TET or salt thereof, and one or more SNRI. The pharmaceuticals, compositions, kits, and methods can protect against noise-induced hearing loss, reduce transmission of abnormal sounds and auditory sensations associated with tinnitus, reduce fluid accumulation in the inner ear, facilitate central auditory processing of sounds and speech, or combinations thereof, comprising administering TET or salt thereof and one or more SNRI, e.g. milnacipran or bicifadine. Milnacipran and bicifadine can be serotonin-norepinephrine reuptake inhibitors, weak N-methyl-D-aspartate antagonists, which improve auditory processing (NSRI activity) and provide protection to inner ear hair cells (NMDA antagonist activity). Milnacipran, bicifadine or a combination of both can provide both central and peripheral benefits to the treated mammal.

In some cases, SNRI (e.g. milnacipran, bicifadine) and TET or salt thereof are combined in the same dosage form. In particular cases, SNRI (e.g. milnacipran, bicifadine) and TET or salt thereof are mixed together. In other cases, SNRI (e.g. milnacipran, bicifadine) and TET or salt thereof are combined with one or more excipients to form a biphasic dosage form, wherein SNRI (e.g. milnacipran, bicifadine) and TET or salt thereof occupy separate phases.

In other cases, SNRI (e.g. milnacipran, bicifadine) and TET or salt thereof are administered in separate dosage forms. In particular cases, the separate dosage forms are administered simultaneously or substantially simultaneously (e.g. within about 10 minutes of one another, more particularly within about 5 minutes of one another, even more particularly within about 2 minutes of one another). In other cases, the separate dosage forms are administered at substantially different times (e.g. more than about 10 minutes apart, more particularly more than about an hour apart). The dosage forms can include those that are currently or presently commercially available, as well as those available to the person having skill in the art. They can include tablets, capsules, caplets, gel caps, powders, solutions, etc.

In some cases, the separate dosage forms of SNRI (e.g. milnacipran, bicifadine) and TET or salt thereof are provided in a kit, such as is defined in more detail below. In specific cases, the separate dosages are provided in a kit including instructions for the administration of SNRI (e.g. milnacipran, bicifadine) and TET or salt thereof for the prevention or treatment of a hearing disorder, especially for the prevention or treatment of hearing loss, tinnitus or both.

TET or Salt Thereof & Calcium Channel Blockers (CCB) and/or Norepinephrine Selective Reuptake Inhibitors (NSRI)

Disclosed herein are pharmaceuticals, compositions, kits, and methods of preventing or treating a hearing disorder by administering TET or salt thereof, e.g. therapeutically effective amount of TET or salt thereof, and one or more CCB and/or NSRI. The pharmaceuticals, compositions, kits, and methods can protect against noise-induced hearing loss, reduce transmission of abnormal sounds and auditory sensations associated with tinnitus, reduce fluid accumulation in the inner ear, facilitate central auditory processing of sounds and speech, or combinations thereof, comprising administering TET or salt thereof and one or more CCB and/or NSRI. Calcium channel blockers/antagonists can provide protection against noise-induced loss and damage of hair cells within the cochlea of the inner ear. Selective serotonin reuptake inhibitors, norepinephrine-serotonin reuptake inhibitors and monoamineoxidase-A inhibitors can enhance central auditory processing.

In some cases, CCB and/or NSRI and TET or salt thereof are combined in the same dosage form. In particular cases, CCB and/or NSRI and TET or salt thereof are mixed together. In other cases CCB and/or NSRI and TET or salt thereof are combined with one or more excipients to form a biphasic dosage form, wherein CCB and/or NSRI and TET or salt thereof occupy separate phases.

In other cases, CCB and/or NSRI and TET or salt thereof are administered in separate dosage forms. In particular cases, the separate dosage forms are administered simultaneously or substantially simultaneously (e.g. within about 10 minutes of one another, more particularly within about 5 minutes of one another, even more particularly within about 2 minutes of one another). In other cases, the separate dosage forms are administered at substantially different times (e.g. more than about 10 minutes apart, more particularly more than about an hour apart). The dosage forms can include those that are currently or presently commercially available, as well as those available to the person having skill in the art. They can include tablets, capsules, caplets, gel caps, powders, solutions, etc.

In some cases, the separate dosage forms of CCB and/or NSRI and TET or salt thereof are provided in a kit, such as is defined in more detail below. In specific cases, the separate dosages are provided in a kit including instructions for the administration of CCB and/or NSRI and TET or salt thereof for the prevention or treatment of a hearing disorder, especially for the prevention or treatment of hearing loss, tinnitus or both.

TET & 5HT Serotonin Reuptake Inhibitor (5HT SRI)

Disclosed herein are pharmaceuticals, compositions, kits, and methods of preventing or treating a hearing disorder by administering TET or salt thereof, e.g. therapeutically effective amount of TET or salt thereof, and one or more 5HT SRI. The pharmaceuticals, compositions, kits, and methods can protect against noise-induced hearing loss, reduce transmission of abnormal sounds and auditory sensations associated with tinnitus, reduce fluid accumulation in the inner ear, facilitate central auditory processing of sounds and speech, or combinations thereof, comprising administering TET or salt thereof and one or more 5HT SRI, such as indeloxazine. Indeloxazine can be a 5HT serotonin reuptake inhibitor, a norepinephrine reuptake inhibitor, an acetylcholine releaser, and an antagonist of N-methyl-D-aspartate. The ability of indeloxazine to increase brain serotonin, norepinephrine, and acetylcholine levels can improve auditory processing, speech recognition and hearing perception.

The ability of indeloxazine to block N-methyl-D-aspartate receptors and to act as an antioxidant can provide protection to the inner ear cells.

In some cases, 5HT SRI (e.g. indeloxazine) and TET or salt thereof are combined in the same dosage form. In particular cases, 5HT SRI (e.g. indeloxazine) and TET or salt thereof are mixed together. In other cases 5HT SRI (e.g. indeloxazine) and TET or salt thereof are combined with one or more excipients to form a biphasic dosage form, wherein 5HT SRI (e.g. indeloxazine) and TET or salt thereof occupy separate phases.

In other cases, 5HT SRI (e.g. indeloxazine) and TET or salt thereof are administered in separate dosage forms. In particular cases, the separate dosage forms are administered simultaneously or substantially simultaneously (e.g. within about 10 minutes of one another, more particularly within about 5 minutes of one another, even more particularly within about 2 minutes of one another). In other cases, the separate dosage forms are administered at substantially different times (e.g. more than about 10 minutes apart, more particularly more than about an hour apart). The dosage forms can include those that are currently or presently commercially available, as well as those available to the person having skill in the art. They can include tablets, capsules, caplets, gel caps, powders, solutions, etc.

In some cases, the separate dosage forms of 5HT SRI (e.g. indeloxazine) and TET or salt thereof are provided in a kit, such as is defined in more detail below. In specific cases, the separate dosages are provided in a kit including instructions for the administration of 5HT SRI (e.g. indeloxazine) and TET or salt thereof for the prevention or treatment of a hearing disorder, especially for the prevention or treatment of hearing loss, tinnitus or both.

TET & Zonisamide

Disclosed herein are pharmaceuticals, compositions, kits, and methods of preventing or treating a hearing disorder by administering TET or salt thereof, e.g. therapeutically effective amount of TET or salt thereof, and zonisamide. The pharmaceuticals, compositions, kits, and methods can protect against noise-induced hearing loss, reduce transmission of abnormal sounds and auditory sensations associated with tinnitus, reduce fluid accumulation in the inner ear, facilitate central auditory processing of sounds and speech, or combinations thereof, comprising administering TET or salt thereof and zonisamide. Zonisamide (1,2-benzisoxazole-3-methanesulfonamide) can complement the pharmacology of a norepinephrine-epinephrine reuptake inhibitor (NERI) by: 1) enhancing serotonin (5HT) and dopamine (DA) transmission; and/or 2) by blocking sodium ($Na^+$) and calcium ($Ca^{++}$) channels. These actions can enhance the efficacy of NERIs in the treatment of depression, schizophrenia, anxiety disorders, sleep-related breathing disorders, snoring, insomnia, migraine headache, chronic tension-type headache, hot flashes, lower back pain, neuropathic pain, functional somatic syndromes and obesity.

In some cases, zonisamide and TET or salt thereof are combined in the same dosage form. In particular cases, zonisamide and TET or salt thereof are mixed together. In other cases, zonisamide and TET or salt thereof are combined with one or more excipients to form a biphasic dosage form, wherein zonisamide and TET or salt thereof occupy separate phases.

In other cases, zonisamide and TET or salt thereof are administered in separate dosage forms. In particular cases, the separate dosage forms are administered simultaneously or substantially simultaneously (e.g. within about 10 minutes of one another, more particularly within about 5 minutes of one another, even more particularly within about 2 minutes of one another). In other cases, the separate dosage forms are administered at substantially different times (e.g. more than about 10 minutes apart, more particularly more than about an hour apart). The dosage forms can include those that are currently or presently commercially available, as well as those available to the person having skill in the art. They can include tablets, capsules, caplets, gel caps, powders, solutions, etc.

In some cases, the separate dosage forms of zonisamide and TET or salt thereof are provided in a kit, such as is defined in more detail below. In specific cases, the separate dosages are provided in a kit including instructions for the administration of zonisamide and TET or salt thereof for the prevention or treatment of a hearing disorder, especially for the prevention or treatment of hearing loss, tinnitus or both.

In some cases, TET or salt thereof can be combined with drugs for treating chronic pains, particularly for tinnitus.

TET & Gabapentin

Disclosed herein are pharmaceuticals, compositions, kits, and methods of preventing or treating a hearing disorder by administering TET or salt thereof, e.g. therapeutically effective amount of TET or salt thereof, and gabapentin. The pharmaceuticals, compositions, kits, and methods can protect against noise-induced hearing loss, reduce transmission of abnormal sounds and auditory sensations associated with tinnitus, reduce fluid accumulation in the inner ear, facilitate central auditory processing of sounds and speech, or combinations thereof, comprising administering TET or salt thereof and gabapentin. Gabapentin can modify voltage gated calcium channels and gamma-aminobutyric acid (GABA) receptors. In some cases gabapentin in combination with TET or salt thereof can produce more profound effects in ameliorating a hearing disorder.

In some cases, gabapentin and TET or salt thereof are combined in the same dosage form. In particular cases, gabapentin and TET or salt thereof are mixed together. In other cases, gabapentin and TET or salt thereof are combined with one or more excipients to form a biphasic dosage form, wherein gabapentin and TET or salt thereof occupy separate phases.

In other cases, gabapentin and TET or salt thereof are administered in separate dosage forms. In particular cases, the separate dosage forms are administered simultaneously or substantially simultaneously (e.g. within about 10 minutes of one another, more particularly within about 5 minutes of one another, even more particularly within about 2 minutes of one another). In other cases, the separate dosage forms are administered at substantially different times (e.g. more than about 10 minutes apart, more particularly more than about an hour apart). The dosage forms can include those that are currently or presently commercially available, as well as those available to the person having skill in the art. They can include tablets, capsules, caplets, gel caps, powders, solutions, etc.

In some cases, the separate dosage forms of gabapentin and TET or salt thereof are provided in a kit, such as is defined in more detail below. In specific cases, the separate dosages are provided in a kit including instructions for the administration of gabapentin and TET or salt thereof for the prevention or treatment of a hearing disorder, especially for the prevention or treatment of hearing loss, tinnitus or both.

TET & *Cannabis*

Disclosed herein are pharmaceuticals, compositions, kits, and methods of preventing or treating a hearing disorder by administering TET or salt thereof, e.g. therapeutically effective amount of TET or salt thereof, and cannabinoid. For example, a cannabinoid can be marijuana or any extract of marijuana or synthetic composition that can stimulate the cannabinoid receptor, CB1 receptor, CB2 receptor, or a G-coupled receptor. A cannabinoid can be *cannabis*, pure *cannabis* extract, or synthetic *cannabis*. The pharmaceuticals, compositions, kits, and methods can protect against noise-induced hearing loss, reduce transmission of abnormal sounds and auditory sensations associated with tinnitus, reduce fluid accumulation in the inner ear, facilitate central auditory processing of sounds and speech, or combinations thereof, comprising administering TET or salt thereof and cannabinoid. Cannabinoids are G-protein coupled receptors. They also modulated the mu and delta opioid receptors so that it is used to treat neuropathic pain and rheumatoid arthritis.

In some cases, cannabinoid and TET or salt thereof are combined in the same dosage form. In particular cases, cannabinoid and TET or salt thereof are mixed together. In other cases, cannabinoid and TET or salt thereof are combined with one or more excipients to form a biphasic dosage form, wherein cannabinoid and TET or salt thereof occupy separate phases.

In other cases, cannabinoid and TET or salt thereof are administered in separate dosage forms. In particular cases, the separate dosage forms are administered simultaneously or substantially simultaneously (e.g. within about 10 minutes of one another, more particularly within about 5 minutes of one another, even more particularly within about 2 minutes of one another). In other cases, the separate dosage forms are administered at substantially different times (e.g. more than about 10 minutes apart, more particularly more than about an hour apart). The dosage forms can include those that are currently or presently commercially available, as well as those available to the person having skill in the art. They can include tablets, capsules, caplets, gel caps, powders, solutions, etc.

In some cases, the separate dosage forms of cannabinoid and TET or salt thereof are provided in a kit, such as is defined in more detail below. In specific cases, the separate dosages are provided in a kit including instructions for the administration of cannabinoid and TET or salt thereof for the prevention or treatment of a hearing disorder, especially for the prevention or treatment of hearing loss, tinnitus or both.

g. Salts, Stereoisomers, Polymorphs and Derivatives

Although described above with reference specific to compounds, one can also utilize stereoisomers, enantiomers, diastereomers, polymorphs, metabolites, derivates, and/or salts of the active compounds. Examples of therapeutically acceptable salts include, but are not limited to, mineral or organic acid salts of basic residues such as amines, and alkali or organic salts of acidic residues such as carboxylic acids. The therapeutically acceptable salts include the conventional non-toxic salts or the quaternary ammonium salts of the parent compound formed, for example, from non-toxic inorganic or organic acids. Conventional non-toxic salts include those derived from inorganic acids such as hydrochloric, hydrobromic, sulfuric, sulfamic, phosphoric and nitric acid; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic and isethionic acids. The therapeutically acceptable salts can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17th ed. (Mack Publishing Company, Easton, Pa., 1985, p. 1418).

Stereoisomers are compounds made up of the same atoms having the same bond order but having different three-dimensional arrangements of atoms which are not interchangeable. The three-dimensional structures are called configurations. Two kinds of stereoisomers include enantiomers and diastereomers. Enantiomers are two stereoisomers which are non-superimposable mirror images of one another. This property of enantiomers is known as chirality. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981). Diastereomers are two stereoisomers which are not mirror images but also not superimposable. Diastereoisomers have different physical properties and can be separated from one another easily by taking advantage of these differences.

Different polymorphs of the compounds may also be used. Polymorphs are, by definition, crystals of the same molecule having different physical properties as a result of the order of the molecules in the crystal lattice. The polymorphic behavior of drugs can be of crucial importance in pharmacy and pharmacology. The differences in physical properties exhibited by polymorphs affect pharmaceutical parameters such as storage stability, compressibility and density (important in formulation and product manufacturing), and dissolution rates (an important factor in determining bio-availability). Differences in stability can result from changes in chemical reactivity (e.g. differential oxidation, such that a dosage form discolors more rapidly when comprised of one polymorph than when comprised of another polymorph) or mechanical changes (e.g. tablets crumble on storage as a kinetically favored polymorph converts to thermodynamically more stable polymorph) or both (e.g. tablets of one polymorph are more susceptible to breakdown at high humidity).

A prodrug is a covalently bonded substance which releases the active parent drug in vivo.

Prodrugs are prepared by modifying functional groups present in the compound in such a way that the modifications are cleaved, either in routine manipulation or in vivo, to yield the parent compound. Prodrugs include compounds wherein the hydroxy or amino group is bonded to any group that, when the prodrug is administered to a patient, cleaves to form a free hydroxyl or free amino, respectively. Examples of prodrugs include, but are not limited to, acetate, formate and benzoate derivatives of alcohol and amine functional groups.

A metabolite of the above-mentioned compounds results from biochemical processes by which living cells interact with the active parent drug or other formulas or compounds in vivo. Metabolites include products or intermediates from any metabolic pathway.

h. Formulations

The compounds, or therapeutically acceptable salts thereof, or polymorphic variations thereof, can be formulated as pharmaceutical compositions. Such compositions can be administered orally, auricularly, e.g. intratympanically, buccally, intravenously, parenterally, by inhalation spray, rectally, intradermally, transdermally, pulmonary, nasally or topically in dosage unit formulations containing conventional nontoxic therapeutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrastromal injection, or infusion techniques. In an embodiment the composition is administered orally. In an embodiment the composition is administered auricularly, e.g. intratympanically.

Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

The active compounds (or therapeutically acceptable salts thereof) may be administered per se or in the form of a pharmaceutical composition wherein the active compound(s) is in admixture or mixture with one or more therapeutically acceptable carriers, excipients or diluents. Pharmaceutical compositions may be formulated in conventional manner using one or more therapeutically acceptable carriers comprising excipients and auxiliaries which facilitate processing of the active compounds into preparations which can be used therapeutically. Proper formulation is dependent upon the route of administration chosen.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Therapeutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicon dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-O-alanine, sodium N-lauryl-O-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The compounds may be complexed with other agents as part of their being therapeutically formulated. The pharmaceutical compositions may take the form of, for example, tablets or capsules prepared by conventional means with therapeutically acceptable excipients such as binding agents (e.g., acacia, methylcellulose, sodium carboxymethylcellulose, polyvinylpyrrolidone (Povidone), hydroxypropyl methylcellulose, sucrose, starch, and ethylcellulose); fillers (e.g., corn starch, gelatin, lactose, acacia, sucrose, microcrystalline cellulose, kaolin, mannitol, dicalcium phosphate, calcium carbonate, sodium chloride, or alginic acid); lubricants (e.g. magnesium stearates, stearic acid, silicone fluid, talc, waxes, oils, and colloidal silica); and disintegrators (e.g. micro-crystalline cellulose, corn starch, sodium starch glycolate and alginic acid. If water-soluble, such formulated complex then may be formulated in an appropriate buffer, for example, phosphate buffered saline or other physiologically compatible solutions. Alternatively, if the resulting complex has poor solubility in aqueous solvents, then it may be formulated with a non-ionic surfactant such as TWEEN™, or polyethylene glycol. Thus, the compounds and their physiologically acceptable solvates may be formulated for administration.

Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation by the patient.

Delayed release and extended release compositions can be prepared. The delayed release/extended release pharmaceutical compositions can be obtained by complexing drug with a therapeutically acceptable ion-exchange resin and coating such complexes. The formulations are coated with a substance that will act as a barrier to control the diffusion of the drug from its core complex into the gastrointestinal fluids. Optionally, the formulation is coated with a film of a polymer which is insoluble in the acid environment of the stomach, and soluble in the basic environment of lower GI tract in order to obtain a final dosage form that releases less than 10% of the drug dose within the stomach.

In addition, combinations of immediate release compositions and delayed release/extended release compositions may be formulated together.

In some cases, TET or salt thereof is formulated as the sole active pharmaceutical ingredient (API) in a dosage form. Such TET or salt thereof dosage form may be used alone or in combination therapy with one or more additional dosages containing one or more active pharmaceutical ingredients for prevention or treatment of hearing loss. In such cases, the daily dosage of TET or salt thereof is conveniently provided in a single dosage form as described herein, or may be divided amongst two, three, four or more dosages.

i. Kits

As discussed above, in some cases, one or more active pharmaceutical ingredients, e.g., two or more APIs, may be co-administered to a mammal for the prevention or treatment of a hearing disorder. In particular, TET or salt thereof may be co-administered with or more additional active pharmaceutical ingredients, such as amantadine, milnacipran, bicifadine, antioxidants or spin trapping agents, NMDA antagonists, SSRI NMDA antagonist compounds, or combinations of at least one SSRI and at least one NMDA antagonist. In other cases, pirlindole may be co-administered along with an antagonist of NMDA or amantadine for the prevention or treatment of a hearing disorder. In still further cases, a calcium channel antagonist may be co-administered along with a SSRI or a NSRI. In further cases, indeloxazine may be used in combination with an antagonist of NMDA. In such cases, it is advantageous to make the specific drug combination available in the form of a kit.

A kit according to the invention includes at least one dosage forms, e.g., two or more dosage forms. For example, the kit can comprise a first active pharmaceutical ingredient and another API comprising at least a second active pharmaceutical ingredient, other than the first active pharmaceutical ingredient. In some cases, the kit includes sufficient doses for a period of time. In particular cases, the kit includes a sufficient dose of each active pharmaceutical ingredient for a day, a week, 14 days, 28 days, 30 days, 90 days, 180 days, a year, etc. In some specific cases, the each dose is physically separated into a compartment, in which each dose is segregated from the others.

In some cases, the kit according to the invention includes at least two dosage forms, one comprising TET or salt thereof and the other comprising at least one active pharmaceutical ingredient other than TET or salt thereof. In some cases, the kit includes sufficient doses for a period of time. In particular cases, the kit includes a sufficient dose of each active pharmaceutical ingredient for a day, a week, 14 days, 28 days, 30 days, 90 days, 180 days, a year, etc. In some specific cases, the each dose is physically separated into a compartment, in which each dose is segregated from the others.

In some cases, the kit can contain one or more APIs, in a form that requires further processing. For example, the one or more APIs can be in powder form and the kit can contain a solution that is used to recombine the power with the solution, e.g., 0.9% NaCl solution. In some case, this reconstituted powder solution can be placed into the ear at various locations. In some cases, the powder is contained into a container that can be used as an applicator.

In particular cases, the kit may advantageously be a blister pack. Blister packs are known in the art, and generally include a clear side having compartments (blisters or bubbles), which separately hold the various doses, and a backing, such as a paper, foil, paper-foil or other backing, which is easily removed so that each dose may be separately extracted from the blister pack without disturbing the other doses. In some cases, the kit may be a blister pack in which each day's dose of a first active pharmaceutical ingredient and at least a second active pharmaceutical ingredient are segregated from the other doses in separate blisters or bubbles. In some such cases, the blister pack may have perforations, which allow each daily dose to be separated from the others by tearing it away from the rest of the blister pack. The separate dosage forms may be contained within separate blisters. Segregation of the two active pharmaceutical ingredients into separate blisters can be advantageous in that it prevents separate dosage forms (e.g. tablet and capsule) from contacting and damaging one another during shipping and handling. Additionally, the separate dosage forms can be accessed and/or labeled for administration to the patient at different times.

In some cases, the kit may be a blister pack in which each day's dose of TET or salt thereof and at least one other active pharmaceutical ingredient is segregated from the other doses in separate blisters or bubbles. In some such cases, the blister pack may have perforations, which allow each daily dose to be separated from the others by tearing it away from the rest of the blister pack. The separate dosage forms may be contained within separate blisters. For example, when TET or salt thereof is to be co-administered with riluzole, a specific number of daily doses may be divided into separate removable daily segments, each segment having at least blister containing TET or salt thereof (e.g. a 25, 50 or 100 mg capsule of TET or salt thereof) and at least one other blister containing riluzole (e.g. a 50 mg tablet of riluzole), with perforations separating the segment from its neighbor or neighbors. Segregation of the two active pharmaceutical ingredients into separate blisters can be advantageous in that it prevents separate dosage forms (e.g. tablet and capsule) from contacting and damaging one another during shipping and handling. Additionally, the separate dosage forms can be accessed and/or labeled for administration to the patient at different times. For example, TET or salt thereof may cause drowsiness in some patients, and so may be labeled for nighttime administration, whereas other active pharmaceutical ingredients may promote alertness and so may be labeled for daytime administration.

In other cases, the kit may be box having separate compartments with separate lids. For example, a kit may comprise a box having seven compartments, each for a separate day of the week, and each compartment marked to indicate which day of the week it corresponds to. In some specific cases, each compartment is further subdivided to permit segregation of one active pharmaceutical ingredient from another. As stated above, such segregation is advantageous in that it prevents damage to the dosage forms and permits dosing at different times and labeling to that effect.

In some cases, the kit may contain written instructions, in any language, directing a subject to use the contents of the kits in a way to effectively treat a disease. The disease can be preventing and/or treating hearing loss.

It will be understood that kits according to the present invention include those in which the first active pharmaceutical ingredient is selected from the group consisting of TET or salt thereof, amantadine, pirlindole, indeloxazine, calcium channel antagonists, and the second active pharmaceutical ingredient is selected from the group consisting of antioxidants, SSRIs, NSRIs, and antagonists of NMDA. Particular kits combine TET or salt thereof and one or members of the group consisting of allopurinol, glutathione, methionine and L-carnitine, riluzole, caroverine, memantine, magnesium, fluoxetine, sertraline, S-citalopram, alaproclate, milnacipran, bicifadine, nimodipine or verapamil. Other kits combine amantadine and one or members of the group consisting of allopurinol, glutathione, methionine and L-carnitine, riluzole, caroverine, memantine, magnesium, fluoxetine, sertraline, S-citalopram, alaproclate, milnacipran, bicifadine, nimodipine or verapamil. Other particular kits combine pirlindole and one or members of the group consisting of allopurinol, glutathione, methionine and L-carnitine, riluzole, caroverine, memantine, magnesium, fluoxetine, sertraline, S-citalopram, alaproclate, milnacipran, bicifadine, nimodipine or verapamil. Still further kits combine indeloxazine and one or members of the group consisting of allopurinol, glutathione, methionine and L-carnitine, riluzole, caroverine, memantine, magnesium, fluoxetine, sertraline, S-citalopram, alaproclate, milnacipran, bicifadine, nimodipine or verapamil. Other kits combine at least one calcium channel antagonist and one or members of the group consisting of allopurinol, glutathione, methionine and L-carnitine, riluzole, caroverine, memantine, magnesium, fluoxetine, sertraline, S-citalopram, alaproclate, milnacipran, bicifadine, nimodipine or verapamil.

j. Treatment Strategies

Disclosed herein are pharmaceuticals, compositions, kits, and methods of treating or preventing a hearing disorder. In some cases, the invention provides a method of treating or preventing noise-induced hearing loss, tinnitus, transmission of abnormal sounds and auditory sensations associated with tinnitus, fluid accumulation in the inner ear, facilitating central auditory processing of sounds and speech, or combinations thereof, comprising administering TET or salt thereof to a mammal in need of such treatment in an amount sufficient to protect against noise-induced hearing loss, reduce transmission of abnormal sounds and auditory sensations associated with tinnitus, reduce fluid accumulation in the inner ear and/or facilitate central auditory processing of sounds and speech. Unless otherwise specified, treatment of one or more of the above hearing disorders is not exclusive of treatment of one or more additional hearing disorders. Moreover, treatment of a hearing disorder is not exclusive of prevention of the same or another hearing disorder, nor is prevention of a hearing disorder exclusive of treatment of the same or another hearing disorder, unless otherwise specified.

In particular cases, the pharmaceuticals, compositions, kits, and methods protect against noise-induced damage or loss of hair cells in the inner cochlea of the inner ear. The method comprises administering TET or salt thereof alone or in combination with one or more additional active ingredients to a mammal in need of protection from noise-induced hearing loss in an amount sufficient to protect against noise-induced hearing loss. In some cases, TET or salt thereof is combined with at least one other active pharmaceutical ingredient, such as an anti-oxidant or spin trapping agent, an NMDA antagonist, a combination of an SSRI and a NMDA antagonist, an agent having both SSRI and NMDA antagonist activity or combinations thereof, in the same dosage form. In other cases, TET or salt thereof is administered to the mammal in a dosage form separate from at least one other active pharmaceutical ingredient, such as an anti-oxidant or spin trapping agent, an NMDA antagonist, a combination of an SSRI and a NMDA antagonist, an agent having both SSRI and NMDA antagonist activity or combinations thereof.

In other cases, the pharmaceuticals, compositions, kits, and methods reduce transmission of abnormal sounds and auditory sensations associated with tinnitus. The method comprises administering TET or salt thereof alone or in combination with one or more additional active ingredients to a mammal in need of reducing transmission of abnormal sounds and auditory sensations associated with tinnitus in an amount sufficient to reduce transmission of abnormal sounds and auditory sensations associated with tinnitus. In some cases, TET or salt thereof is combined with at least one other active pharmaceutical ingredient, such as an anti-oxidant or spin trapping agent, an NMDA antagonist, a combination of an SSRI and a NMDA antagonist, an agent having both SSRI and NMDA antagonist activity or combinations thereof, in the same dosage form. In other cases, TET or salt thereof is administered to the mammal in a dosage form separate from at least one other active pharmaceutical ingredient, such as an anti-oxidant or spin trapping agent, an NMDA antagonist, a combination of an SSRI and a NMDA antagonist, an agent having both SSRI and NMDA antagonist activity or combinations thereof.

In other cases, the invention provides methods of reducing fluid accumulation associated with trauma and other disorders of the inner ear. The method comprises administering TET or salt thereof alone or in combination with one or more additional active ingredients to a mammal in need of reducing fluid accumulation associated with trauma and other disorders of the inner ear in an amount sufficient to reduce fluid accumulation. In some cases, TET or salt thereof is combined with at least one other active pharmaceutical ingredient, such as an anti-oxidant or spin trapping agent, an NMDA antagonist, a combination of an SSRI and a NMDA antagonist, an agent having both SSRI and NMDA antagonist activity or combinations thereof, in the same dosage form. In other cases, TET or salt thereof is administered to the mammal in a dosage form separate from at least one other active pharmaceutical ingredient, such as an anti-oxidant or spin trapping agent, an NMDA antagonist, a combination of an SSRI and a NMDA antagonist, an agent having both SSRI and NMDA antagonist activity or combinations thereof.

In other cases, the pharmaceuticals, compositions, kits, and methods stimulate central nervous system serotonin neurotransmission, thereby facilitate central auditory processing of sounds and speech. The method comprises administering TET or salt thereof alone or in combination with one or more additional active ingredients to a mammal in need of such treatment in an amount sufficient to facilitate central auditory processing. In some cases, TET or salt thereof is combined with at least one other active pharmaceutical ingredient, such as an anti-oxidant or spin trapping agent, an NMDA antagonist, a combination of an SSRI and a NMDA antagonist, an agent having both SSRI and NMDA antagonist activity or combinations thereof, in the same dosage form. In other cases, TET or salt thereof is administered to the mammal in a dosage form separate from at least one other active pharmaceutical ingredient, such as an anti-oxidant or spin trapping agent, an NMDA antagonist, a combination of an SSRI and a NMDA antagonist, an agent having both SSRI and NMDA antagonist activity or combinations thereof.

The pharmaceuticals, compositions, kits, and methods can both protect against hearing loss and treat hearing loss. In this context, protecting against hearing loss means that the active pharmaceutical ingredient or ingredients protect, at least to some degree, against the loss of hearing in a mammal. Such protection may range from slight to nearly complete. The mammal treated may be one that has already experienced hearing loss, including one that has already experienced hearing loss and is expected to be subjected to conditions similar to those that brought about the current degree of hearing loss. The mammal treated may also be one that has yet to experience notable hearing loss but is expected to be at risk for hearing loss, due to genetic profiling, expected exposure to one or more hearing-loss inducing causes (such as excessive noise), or a combination of those factors. In this context, treatment of hearing loss can mean restoring (at least in part) hearing to the mammal, or ameliorating one or more symptoms of hearing loss. Symptoms of hearing loss can include experiencing abnormal sounds and auditory sensations associated with tinnitus and reduced ability to distinguish sounds and/or spoken words.

EXAMPLES

Example 1: Neurotoxicity Evaluation of Chronic TET Use

Animals and Chemicals

CBA/CaJ mice were purchased from The Jackson Laboratory. One to five mice were housed per cage with food and water available in a noise-controlled environment on a 12-hr light/dark cycle with light onset at 6:00 a.m. TET was obtained from Sigma Chemical Co. (St. Louis, Mo.). The drug solution was injected (i.p.) for the treated groups. Control mice were given saline injection only. The amount of water/food intake was monitored daily and body weight was monitored weekly.

Results

Drug neurotoxic effects on sensory motor coordination were assessed on two-month old CBA/CaJ mice using the accelerating rotarod method. Mice were trained on the task for 5 days in order to achieve stable performance before either being treated by intraperitoneal (i.p.) injections with TET at 120 mg/kg body weight (n=5) or saline (n=6). Latency to fall was not significantly different between the control and TET treated animals before or after five days of TET treatment (two-way ANOVA, $p>0.05$) (FIG. 1). Thus, TET treatment at 120 mg/kg for five days did not induce any significant disturbances of sensory motor function.

Example 2: Prophylactic Function of TET Against ARHL

Figure 2:
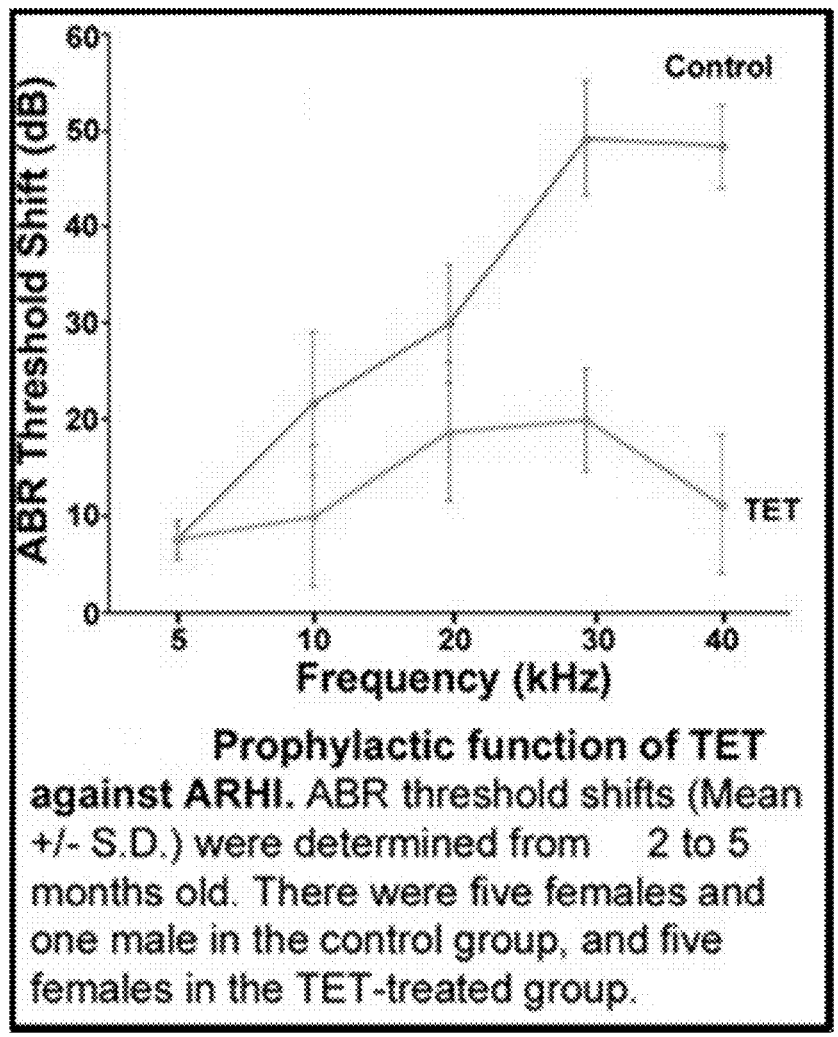
FIG. 2 is a comparison of the ABR threshold shifts against ARHL between the control and TET-treated groups. ABR threshold shifts (Mean+/−S.D.) were determined from 2 to 5 months old. There were five females and one male in the control group, and five females in the TET-treated group.

Currently, no FDA-approved medications against ARHL are available. Two-month old CBA/CaJ mice were exposed to octave band (4-25 kHz) noise at 110 dB SPL for 30 minutes. This is a well-established noise model for our drug screenings since the noise exposure leads to dramatic acute and permanent hearing threshold shifts 24 hours and two weeks post-exposure respectively. In addition, apparently accelerated age-related increase in the auditory brainstem response (ABR) thresholds were observed three months after the noise exposure in the control group (n=6), up to approximately 50 dB at 40 kHz. Mice treated with TET (n=5) three days before and two days after the noise exposure had only about an increase of 10 dB at 40 kHz three months after exposure (FIG. 2). A significant difference between ABR threshold shifts was observed between the control and TET-treated groups (two-way ANOVA, $p<0.001$). Thus, TET treatment at a young age could prevent accelerated age-related hearing loss due to early noise exposure.

Example 3: Determine the Effect of TET on Motor Coordination

Figure 3:
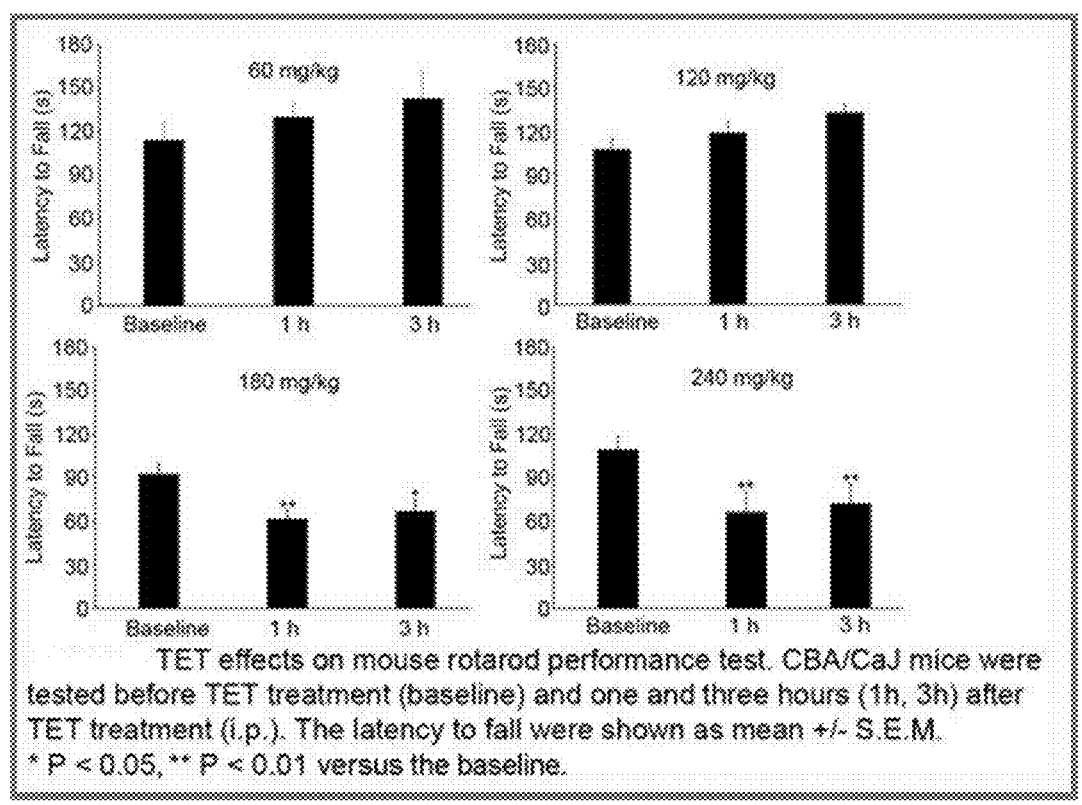
FIG. 3 illustrates the effects of TET on mouse rotarod performance test. CBA/CaJ mice were tested before TET treatment (baseline) and one and three hours (1 h, 3 h) after TET treatment (i.p.). The latency to fall were shown as mean+/−S.E.M.

TET effects on motor coordination were evaluated on the accelerating rotarod test. the rotating speed was increased with an acceleration rate of 10 rpm/min. The length of time that each animal was able to stay on the rod was recorded as the latency to fall. TET was dissolved in 0.1 N HCl at a concentration of 50 mg/ml, and the pH was adjusted to 6.8-7.0 before diluted in saline. Mice were injected intraperitoneally (i.p.) with saline (baseline) or different TET dosages. Rotarod performance was evaluated at 1 and 3 h after injection (FIG. 3). By using a one-tailed t-test, no significant side effects were found for TET at 60 mg/kg (n=7; 5 males), or 120 mg/kg (n=12; 10 males), while a significant difference was observed at 180 mg/kg ($p<0.01$ at 1 h; $p<0.05$ at 3 h; n=10, 8 males) or 240 mg/kg ($p<0.01$ at 1 h; $p<0.01$ at 3 h; n=7, 5 males). No significant gender effect was detected at either time point ($p>0.1$).

Example 4: Determine the Effect of TET on Sensory Gating

Figure 4:
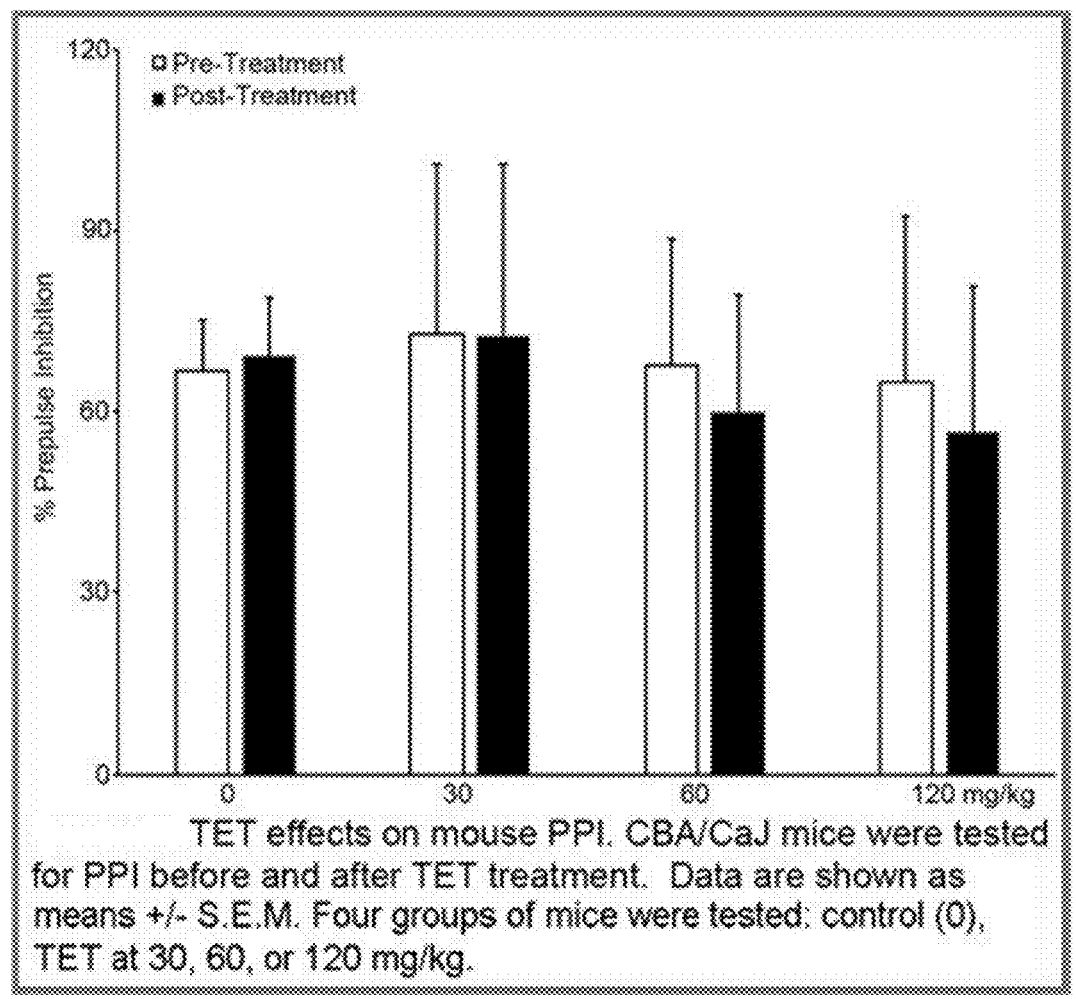
FIG. 4 illustrates the effects of TET on mouse prepulse inhibition (PPI). CBA/CaJ mice were tested for PPI before and after TET treatment. Data are shown as means+/−S.E.M. Four groups of mice were tested: control (0), TET at 30, 60, or 120 mg/kg.

TET effects on sensory gating were evaluated using a prepulse inhibition (PPI) procedure. Mice were placed in a plastic restrainer situated on a plate with a pressure sensor. Any animal motion was detected by the sensor which measured its amplitude. TET at various dosages was injected (i. p.) 1 h before the test. For this study, CBA/CaJ mice were divided into four groups: control with saline injection only (n=6; 2 males), TET at 30 mg/kg (n=6; 3 males), 60 mg/kg (n=10; 5 males) and 120 mg/kg (n=6; 2 males). For all groups, the ratio between the PPI and startle amplitude was measured (FIG. 4). No significant differences were found between the pre- and post-treatment for all four groups or between genders (p>0.05). Thus, TET at 120 mg/kg has no toxic effects on sensory gating in the CBA/CaJ mouse.

Example 5: Determine the Effect of TET on Memory

Figure 5:
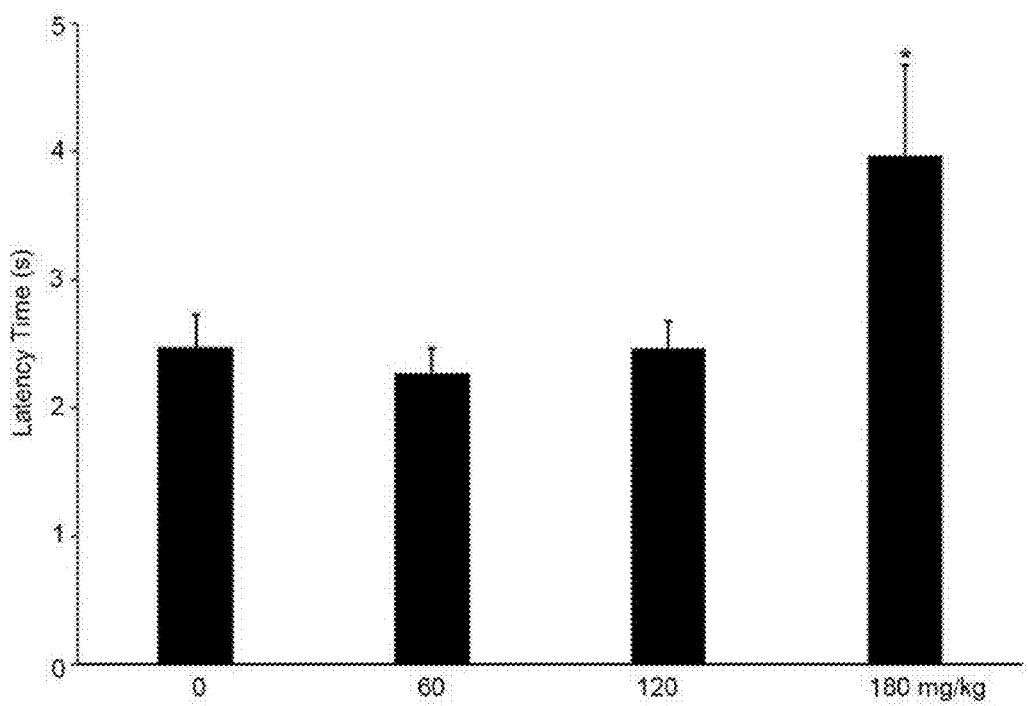
FIG. 5 illustrates the effects of TET on mouse avoidance test. C57BL/6J mice were trained to move in the shuttle box when a sound was present. After 10 days of training, the latency of their avoidance test was recored and compared between the control (0) and drug-treated groups. Data are shown as means+/−S.E.M.

TET effects on memory were evaluated in mice with a rodent avoidance system, which consisted of two compartments of equal size (12.5 cm×20 cm×20 cm) that were connected by a door. Infrared LEDs were used to monitor rodent movement in each compartment. Sound cues were delivered via piezo tweeters in the ceiling of the compartments. Animals were trained to move from one compartment to the other upon presentation of the sound. If they did not move through the door they received a shock. The trials and responses were collected. Behavioral responses of mice with or without TET injection were measured after injection (FIG. 5). No significant difference was observed between the control mice (n=8, 4 males) and mice treated with TET at 60 mg/kg (n=9, 3 males) or 120 mg/kg (n=9, 3 males). A significant increase of latency to cross was observed for mice treated at 180 mg/kg (n=9, 3 males; one-tailed t-test, p<0.05), which could be due to TET effects on mouse memory or motor functions (see FIG. 3). Again, one time administration of TET at 120 mg/kg had no significant toxic effects on memory in mice.

Example 6: Prophylactic Function of TET Against NIHL

Figure 6:
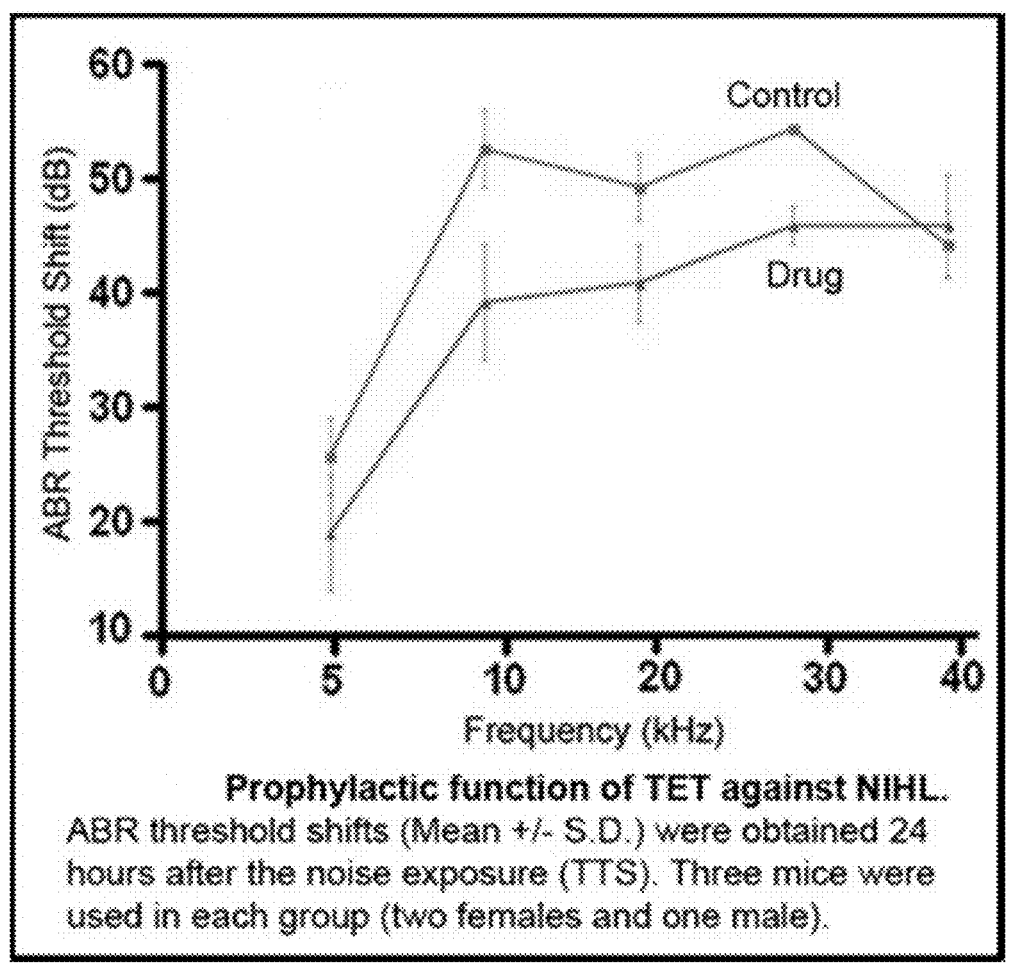
FIG. 6 is a comparison of the ABR threshold shifts against NIHL between the control and TET-treated groups. ABR threshold shifts (Mean+/−S.D.) were obtained 24 hours after the noise exposure (TTS). Three mice were used in each group (two females and one male).

As shown in FIG. 6, it was determined that NIHL can be significantly reduced by TET (120 mg/kg) given two days before and three days after white noise exposure at 110 dB SPL for 30 minutes in four month-old CBA/CaJ mice. The average TTS across all test frequencies was 69.7 dB for the control group, 62.9 dB for the TET-treated group (about 6.8 dB of protection). Two-way ANOVA showed a significant effect of drug concentration (F2=3.32, p=0.04) with no effect of frequency. Tukey post-hoc tests indicated ABR thresholds were significantly different between the drug-treated group and the control group.

Figure 7:
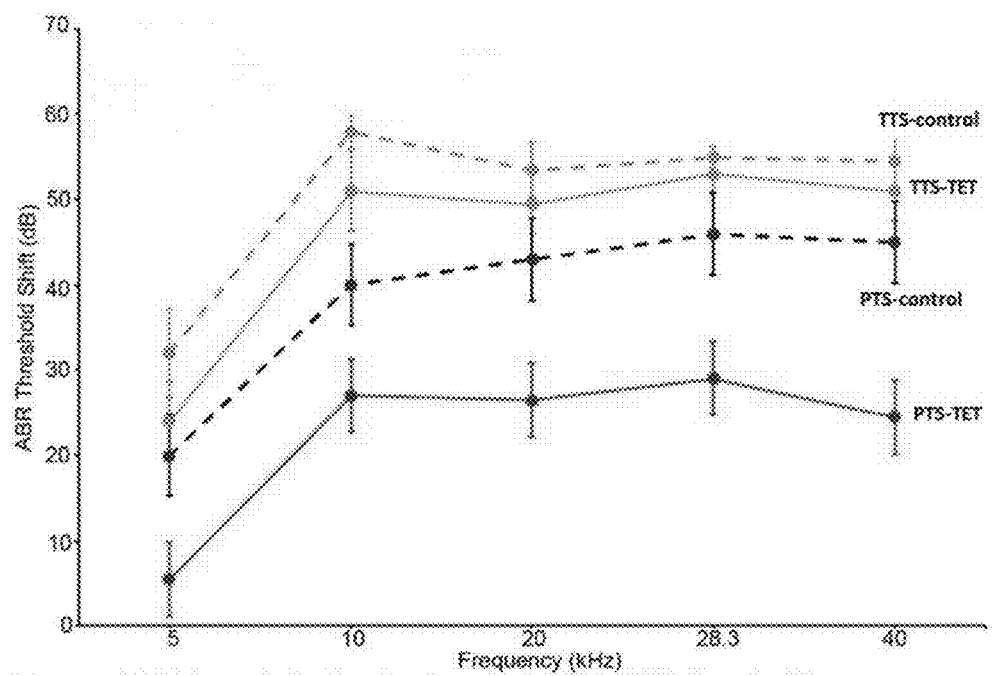
FIG. 7 illustrates the prophylactic effect of TET against NIHL. ABR thresholds were determined one day before, one day after (TTS), and two weeks after (PTS) the noise exposure. TET at 120 mg/kg was injected (i.p.) two hours before the noise exposure. The threshold shifts are shown as means+/−S.E.M.

In another experiment, ABR thresholds of 2 month old CBA/CaJ mice were measured one day before noise exposure (broadband noise, 4-25 kHz, 110 dB SPL for 30 min). TET at 120 mg/kg or saline were injected (i.p.) 2 h before noise exposure. TTS was determined 24 h after exposure and PTS three weeks post-exposure (FIG. 7; n=10, 5 males). One-way ANOVA analysis indicated a significant protection effect for both TTS (F=12.741, p<0.01) and PTS (F=9.577, p<0.01). No significant gender effect was seen for either TTS or PTS (one-way ANOVA, p>0.05).

Figure 8:
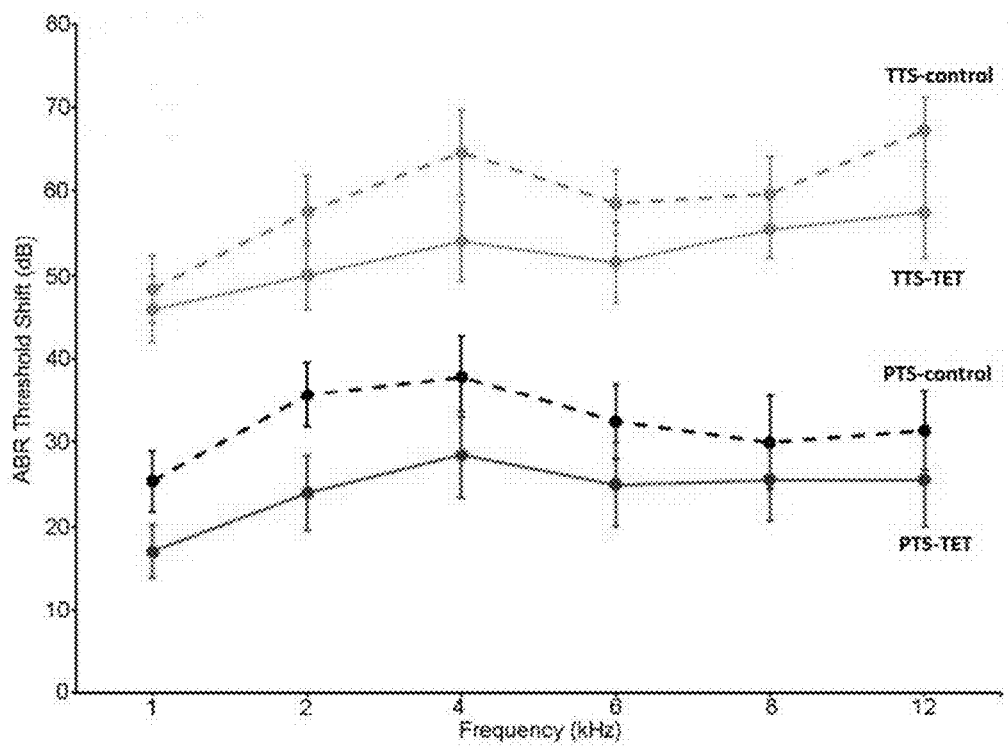
FIG. 8 illustrates the prophylactic effect of TET against NIHL in chinchillas. ABR thresholds were determined one day before, one day after (TTS), and two weeks after (PTS) the noise exposure. TET at 60 mg/kg was injected (i.p.) two hours before the noise exposure. The threshold shifts are shown as means+/−S.E.M.

In yet another experiment, a comparable NIHL model in chinchillas was developed (FIG. 8). ABR thresholds were first determined in adult chinchillas. Similar to our mouse experiments, TET was injected (i.p.) 2 h before the noise exposure (0.5-6 kHz band of noise at 115 dB SPL for 1 h). One-way ANOVA analysis showed significant protection for both TTS (F=7.401, p<0.01) and PTS (F=8.31, p<0.01) with a much lower TET dosage (60 mg/kg).

A detailed pharmacodynamic study in a well-established animal model for ARHL can help us determine whether TET can delay presbycusis. Additionally, because TET side effects are dose-dependent, a detailed study of TET anti-ARHL dosage can result in a less cumbersome transition to clinical trials. The TET dose-effect curve will be established by administering TET to B6 mice from 8 months to 10 months of age. The B6 mouse strain is widely used as a model for presbycusis and provides an efficient timescale for our drug screen. The cochlear aging phenotype of B6 mice appears to be mixed sensory/primary neural presbycusis. ARHL are found to accelerate in these mice between 8-10 months, so the threshold changes in this period can be used as an indicator of efficacy against ARHL.

Example 7: Determine Pharmacodynamics Properties of TET Against ARHL in C57BL/6J Mice A detailed pharmacodynamic study in a well-established animal model for ARHL can help us determine whether TET can delay presbycusis. Additionally, because TET side effects are dose-dependent, a detailed study of TET anti-ARHL dosage can result in a less cumbersome transition to clinical trials. The TET dose-effect curve will be established by administering TET to B6 mice from 8 months to 10 months of age. The B6 mouse strain is widely used as a model for presbycusis and provides an efficient timescale for our drug screen. The cochlear aging phenotype of B6 mice appears to be mixed sensory/primary neural presbycusis. ARHL are found to accelerate in these mice between 8-10 months, so the threshold changes in this period can be used as an indicator of efficacy against ARHL.

Animals and Chemicals

C57BL/6J and CBA/CaJ mice will be purchased from The Jackson Laboratory. One to five mice will be housed per cage with food and water available in a noise-controlled environment on a 12-hr light/dark cycle with light onset at 6:00 a.m. TET will be obtained from Sigma Chemical Co. (St. Louis, Mo.). The drug solution will be injected (i.p.) for the treated groups. Control mice will be given saline injection only. The amount of water/food intake will be monitored daily. Body weight will be monitored weekly.

Noise Exposure

Similar to earlier experiments, noise exposures on 2 month old CBA/CaJ mice will be performed in a foam-lined, soundproof room (Industrial Acoustics). The acoustic overexposure will be octave band noise (8-16 kHz) at 110 dB SPL lasting 30 minutes. Noise will be produced digitally using a TDT RZ6 controlled by custom Labview routines. A 3-second noise loop will be output from the RZ6 to a Crown D75A power amplifier connected to an exponential horn fixed directly over cages from which the isolator tops and bedding are removed. Mice will be exposed singly. The overall noise level will be measured at the center of the space under the speaker using a B&K ½ inch microphone in a combination with a sound level meter set to broadband. Sound levels will be monitored and logged in real time using custom Labview routines.

Auditory Brainstem Response (ABR) Testing

ABR testing will be performed by an operator blinded to experimental condition, with the animals placed in a double-walled soundproof booth (IAC). Mice will be anesthetized with an intramuscular injection of 80 mg/kg ketamine and 5 mg/kg xylazine solution. They will then be positioned dorsally in a custom head holder with their right ear 7.0 cm from the sound source. Body temperature will be maintained at 37.5±1° C. with the use of a controlled heating pad and a rectal probe. Platinum needle electrodes will be inserted subdermally behind the right ear (reference), at the vertex (active), and in the back (ground). ABR threshold at each test frequency will be defined as the lowest stimulus level at which Wave 1 is clearly present, using a 5 dB step size. All thresholds will be verified by repetition at each frequency tested. Stimuli will be 5 ms tone bursts presented at 1,000 times at 5, 10, 20, 30, and 40 kHz. Tucker Davis Technologies System III hardware and BioSigRZ software will be used for stimulus presentation and data acquisition. To construct input-output curves of ABR Wave 1 at 10 kHz, the ABR threshold at 10 kHz for each animal will be determined, and then the amplitude of Wave 1 will be measured using either P1-N1 or P1 peak to baseline. The sound level will be increased in 5 dB steps, with a maximum level of 95 dB SPL.

Statistical Analysis

In addition to determination of $ED_{50}$ as described above, statistical comparisons will entail comparison by group at the determined $ED_{50}$ of ABR thresholds, DPOAEs and ABR Wave I I/O curves. Considerations of sample size will be based on several factors to minimize the number of animals required to achieve the objectives of the study while maintaining the statistical significance of the data. The appropriate number of animals for both Aims will be based on the following factors: difference in means between two groups (effect size), standard deviation (variability of data), significance level ($\alpha$) and power ($1-\beta$). The significance level will be set at alpha=0.05 and the desired power is set at 80% ($\beta$=0.2). The other factors (effect size and variance) will be based on our previous studies. Two-way ANOVA with multiple comparisons testing will be used to characterize differences by group. Gender effects within group will be examined by two-tailed t-test. SigmaStat and SPSS will be used for these analyses.

Experiment Design

A median-effect equation will be used to establish the pharmacodynamics of TET against presbycusis. Saline or TET will be administrated (i.p.) once per day for two months. The ABR threshold assessment will be repeated for the same animals at 10 months old. On the X axis, the dosage range will be established using two steps. Mice will be treated with TET at 120 mg/kg, because this dosage was shown to be effective without obvious toxic effects in our earlier experiments. Three additional concentrations (0.5×, 0.25×, and 0.05×) will also be tested to determine the $ED_{50}$ against ARHL. On the Y axis, the response value (Fa) will be the percentage of average ABR threshold shift between age 8 months (before treatment) and 10 months (after treatment) normalized to the control, as follows:

$$Fa = (ABR@10\text{-Month}_{drug} - ABR@8\text{-Month}_{drug}) \times 100\% / (ABR@10\text{-Month}_{control} - ABR@8\text{-Month}_{control}).$$

(ABR@10-Month–ABR@8-Month) will be the average of the ABR shifts across 5, 10, 20, 30, and 40 kHz. For each compound, based on the statistical analysis detailed above, 30 B6 mice will be needed for one dose-response curve (15 per gender). With four doses per drug plus a control group, a total of 150 B6 mice will be needed. Possible gender differences of TET will be monitored in this project. A two-way ANOVA test will be used to determine if there is a gender difference for TET anti-ARHL activities. The dose-response curve will be established using CompuSyn software (ComboSyn, Inc.).

Results

The TET anti-ARHL $ED_{50}$ will be determined. It will also be beneficial to explore the underlying cellular and molecular mechanisms so that future translational approaches can be improved. Therefore, after the most effective TET concentration is identified, two additional functional assays will be used to determine possible involvement of outer hair cells (OHCs), and synapses between inner hair cells (IHCs) and spiral ganglion neurons (SGNs). Distortion-product otoacoustic emissions (DPOAEs) will be used to monitor effects on the function of OHCs. ABR wave 1 input-output curves will be used to determine if the drug treatment acts on IHC/SGN synapse, as the ABR Wave 1 represents the summed activity of the cochlear nerve, and the input-output relation for wave 1 is acutely sensitive to the IHC/SGN synaptic strength and the number of responding neurons.

Example 8: Determine TET Anti-ARHL Pharmacodynamics Properties in CBA/CaJ Mice

In addition to B6 mice, CBA/CaJ mice will also be tested since an early noise-induced ARHL model is established in this strain. This model will provide another efficient system for ARHL drug screenings, and overcomes the otherwise slow progression of ARHL in CBA/CaJ mice. ABR thresholds for CBA/CaJ mice at 2 months old will be determined and the animals will be subsequently exposed to white noise (4 to 25 kHz) at 110 dB SPL for 30 minutes. ABR testing will be repeated at 5 months old.

Experiment Design

Experimental procedures and methods will be similar to the above examples. Two different TET dose-response curves will be established based on the timing of TET administration in regard to the noise exposure. For the first curve, TET will be administrated three days before and two days after the noise exposure. In the second dose-response analysis, TET will be administrated for two months, starting two weeks after the noise exposure. This test is aimed at real-world conditions involving delayed treatment after exposure. Similar to the experiments proposed in Example 3, TET at four dosages (120, 60, 30 and 6 mg/kg) will be administered (i.p.). Dose-response curves will be generated using CompuSyn software (ComboSyn, Inc.). The TET anti-ARHL $ED_{50}$ will be obtained. A total of 300 CBA/CaJ mice will be used to establish these two dose-response curves (150 mice per curve, each curve with five dosages×30 animals, 15 per gender for each dosage).

Results

TET $ED_{50}$ for at least one administration regimen will be identified. Additional preclinical data for the IND application will also be generated. At the same time, DPOAEs and ABR wave 1 input-output curves will be used to determine possible cellular targets for TET in this animal model.

Example 9: Prophylactic and Therapeutic Function of TET Against NIHL

There are currently no preventative medications effective against NIHL. With multiple molecular pathways involved in NIHL, plan to determine the prophylactic and therapeutic function of TET against NIHL, for example, to determine whether TET can effectively prevent NIHL.

Animals and Drug Treatments.

CBA/CaJ mice at 4 months old will be purchased from Jackson Laboratories. Five mice will be housed per cage with food and water available in a noise-controlled environment on a 12-hr light/dark cycle with light onset at 6:00 a.m. Mice will be randomly assigned to either treated or untreated groups. The treatment drugs will be injected (i.p.). The control groups will be injected with normal saline.

NIHL Model

Noise exposures will be performed in a double-walled soundproof room (Industrial Acoustics). Broadband noise (4-25 kHz) will be generated using custom written LabVIEW software and routed through a Crown CDi1000 power amplifier to a Selenium D3500Ti—Nd loudspeaker.

The overall noise level is measured at the center of the cage using B&K 4153 ¼ inch microphone connected to a B&K *Nexus* broadband conditioner amplifier (1-100,000 Hz) and monitored using custom written software. For the studies in this project, mice and chinchillas will be exposed to white noise at 110 dB SPL (+/−2 dB) for 30 min in pairs housed within a divided cage.

ABR Assay

The cochlea can respond to frequencies ranging from 2 to 100 kHz and can be most sensitive around 5 to 40 kHz. Therefore, test at 5, 10, 14.2, 20, 28.3, and 40 kHz will be covered. The "near field" sound stimulation and calibration will be used in which the speaker is near the ear (7 cm) within the range where the sound field is approximately homogeneous within an imaginary cylinder surrounding the ear. To make sure sound stimuli are constant from animal to animal, a B&K 4135 ¼ inch microphone is placed where the mouse ear would normally be and calibrated before the experiment. Prior to testing, all mice and chinchillas will be anesthetized with pentobarbital (60 mg/kg, i.p.) and given atropine sulfate (0.5 mg/kg, i.p.) to reduce respiratory distress. Otoscopic examination will be performed to ensure that tympanic membranes are normal. Core temperature will be maintained at 37+/−1° C. using a thermostatically-controlled heating pad in conjunction with a rectal probe (Yellow Springs Instruments, Model 73A). Platinum needle electrodes (Grass) will be inserted subcutaneously just behind the right ear (active), and at the vertex (reference), and in the back (ground).

Alternating phase toneburst stimuli (5 ms duration, 0.5 ms rise/fall time) will be generated using commercially available software (SigGenRZ version 5.1) from Tucker Davis Technologies (TDT) and presented at a rate of 20/sec. Responses will be amplified with a gain of 20,000 using a headstage (TDT RA4LI) connected to a preamplifier (TDT RA4PA) and bandpass filtered from 100-3000 Hz. 512 sweeps will be averaged at each stimulus frequency and level using TDT BioSigRZ version 5.1. Thresholds will be defined as the lowest sound pressure level that a detectable and repeatable Wave I can be detected using a 5 dB step size.

Behavior Tests

The accelerating rotarod test will be performed on the Economex (Columbus Instruments, OH) for two days with six trials each day. In every trial, the mice and chinchillas will be placed on top of the rod. One minute later, the rod will be rotated at 5 rpm with acceleration rate of 5 rpm. The holding latencies will be recorded. The Morris water maze test will be performed under three water maze testing conditions (Cue, Place, and Random conditions), differing from escape platform visibility and/or location, will be studied. Each of the six-day sessions will be composed of twelve 1-min acquisition (learning) trials, followed by a single 1-min probe (memory) trial. During learning trials, latency to locate the platform (i.e., escape latency: time from release until all four paws are on the platform) will be measured in seconds, with a time limit of 60 seconds. During memory trials (no escape platform in the maze), the time that the mouse spends in the "probe" quadrant (the area that previously contained the platform during the learning phase) will be measured as probe time in seconds, with time limit of 60 seconds.

Example 10: Determine the Effect of TET Treatment 12 Hours after the Noise Exposure in Diminishing NIHL TET treatment 12 hours post-exposure is useful in clinical applications. Similar to example 7, the TET dose-effect curve will first be established to obtain its ED50 against NIHL. The ABR thresholds of animals will be measured one day before the noise exposure and TET will be injected (i.p.) 12 hours post-exposure. TTS will be measured 24 hours post-exposure and PTS will be measured three weeks post-exposure. The dose-effect curve will be obtained by the CompuSyn software for both TTS and PTS. Along the x axis, the dosage range will be decided by expanding the initial dosage of 120 mg/kg (see Preliminary Data) with at least four concentration points (2×, 0.5×, 0.1× and 0.25×) to determine the TET $ED_{50}$ (median effective dose) against NIHL. If no protection is observed, the dosage will be expanded in log units to search for dosages with protective effects.

The result of this experiment will assist us to explore the protective mechanisms of TET against NIHL. For example, if the dose-response curve for TTS is similar between this experiment and the experiment in example 7, it may suggest that the protection against NIHL by this drug occurs mainly after the noise exposure (the TTS phase). On the other hand, if the $ED_{50}$ for TTS from example 7 is much lower than the $ED_{50}$ for this experiment, the data may suggest that the protective nature of this drug is at least partly due to preconditioning.

Example 11: Determine the Effect of TET Treatment for NIHL Intervention

This example demonstrated that tetrandrine, a potent calcium blocker with anti-oxidative and anti-inflammatory effects, significantly attenuated noise-induced hearing loss in rodent model of NIHL. A single dose of tetrandrine administrated before noise exposure showed a significant protective on permanent threshold shift in both models.

Animals

A total of 66 two-month-old CBA/CaJ mice obtained from Jackson Laboratory (Bar Harbor, Me., USA) were used in the experiments. A mix of males and females were used across experiments. All animals were allowed free access to food and water. They were maintained in a temperature-, humidity- and light-controlled environments on a 12 h light-dark cycle with light onset at 6:00 am.

Drug Application

Tetrandrine (TET, C38H4206N2, molecular weight: 622.8 g/mol) was purchased from ABCAM, USA. TET powder was dissolved in 0.01 M hydrogen chloride (HCl), and the pH was adjusted to 6.5 with 0.01 M Sodium hydroxide (NaOH). The control solution was made with HCL and NaOH, and the pH was adjusted to 6.5. The mice exposed to noise were randomized into seven groups with both genders: five drug groups and two control groups. The five drug groups were: TET80, TET100, TET120, the prevent group, and the treatment group. For the TET80, TET100, and TET120 groups, the mice were injected once per day for five consecutive days: two days before noise exposure, the day of the noise exposure, and two days after with 80, 100, or 120 mg/kg TET per injection. For the prevent group, the mice received a single injection of 120 mg/kg TET two hours before noise exposure. For the treatment group, mice received a single injection of 120 mg/kg TET immediately after noise exposure. Two control groups were treated with one or five vehicle injections over the same schedules as the drug groups.

Auditory Brainstem Response (ABR)

Mouse ABR testing was conducted in soundproof booths prior to drug administration and noise exposure to establish pre-exposure auditory sensitivity. Twenty-four hours and 15 days after noise exposure, ABR testing was repeated to assess temporary threshold shift (TTS) and permanent threshold shift (PTS). Mice were anesthetized with 100 mg/kg ketamine and 10 mg/kg xylazine (i.p.) and placed on a thermostatically-controlled heating pad in conjunction with a rectal probe (Yellow Springs Instruments Model 73A). Three platinum recording electrodes were inserted subcutaneously posterior to the right pinna (active), vertex (reference) and in the back (ground). The acoustical stimulus generation, ABR wave acquisition, equipment control, and data management were confirmed using a Tucker Davis Technologies (TDT, Alachua, Fla.) RZ6 Multi I/O processor and BioSigRZ software. A B&K 4135 ¼ inch speaker was placed at 10 cm distance from the right ear of each animal. Tone burst stimuli (5 ms duration, 0.5 ms rise/fall time) from 2 to 20 kHz were presented 1000 times in 20/sec at frequencies of 5, 10, 20, 28.3, 40 kHz. Starting level was typically 90 dB SPL, with decrease in 5 dB steps. Thresholds were determined as the lowest sound pressure level that a detectable and repeatable ABR wave can be judged at each frequency using a 5 dB minimum step size. The ABR wave-1 was identified and the peak to peak amplitude was calculated by off-line computed analysis of stored waveforms using a written program in Matlab software. ABR wave-1 amplitudes were averaged as groups at 5, 10, 20, 28.3 and 40 kHz.

Distortion Product Otoacoustic Emissions (DPOAEs)

In addition to ABR testing in the mice, DPOAEs were collected. DPOAE recording was conducted in the same booth used in ABR test and scheduled to follow ABR test. The primary tones f1 and f2 were generated and shaped using EMAV software (Neely & Liu, 1995) and TDT hardware. DPOAEs were recorded in the form of level/frequency functions, f2/f1 was fixed as 1.2, with the level of the f2 (L2) 10 dB less than f1 level (L1). L2 was fixed at one level, and f2 frequencies were swept from 6-40 kHz in 1/10th octave steps. The 2f1-f2 DPOAE amplitude and surrounding noise floor were extracted. The signal coming from the ear canal was collected by a modified Knowles low noise microphone and custom pre-amplifier.

Noise Exposure

Awake mice were exposed two at a time in divided cages in a foam-lined, double-walled soundproof room (Industrial Acoustics). Broadband noise (4-25 kHz) was generated using custom written LabVIEW software and routed through a power amplifier (Crown CDi1000) to a loudspeaker (Selenium D3500Ti—Nd). The overall noise level was measured at the center of the cage using B&K 4153 ¼ inch microphone connected to a broadband conditioner amplifier (1-100,000 Hz; Bruel & Kjaer Nexus Amplifier) and monitored using custom written software.

Before each noise exposure, noise levels were calibrated to 110 dB SPL (+/−1 dB).

All subjects including control animals were exposed to broadband noise (4-25 kHz, 110 dB SPL) for 30 min.

Cochlear Tissue Preparation and Immunostaining Procedure

After the final ABR and DPOAE measurement, the deeply anesthetized mice were perfused with cold 4% paraformaldehyde in 0.1 M phosphate buffer. Then the cochleae were immediately isolated and immersed in the same fixative solution. Completed fixed for 1-2 h, the cochlea was decalcified in 0.35M EDTA for 2 days. The cochlea was microdissected into six pieces. Dissected pieces were dehydrated in 30% sucrose, frozen in dry ice for 10 min. Thawed samples were washed 3 times in 0.01 mM PBS and pre-incubated for 1 h in PBS blocking buffer (0.05% Triton X-100, 5% normal horse serum) at room temperature. Cochleae pieces were incubated with primary antibodies to the following: (1) C-terminal binding protein 2 (mouse anti-CtBP2; BD Transduction Labs, used at 1:200), (2) myosin-VIIa (rabbit anti-myosin-VIIa; Proteus Biosciences, used at 1:200), with matching secondary antibodies (Life Technologies, USA) and coupled to Alexa Fluors in the red, blue, and green channels (Fernandez K A, 2015). Stained cochlear pieces were mounted on slides with the medium: Fluoromount-G (SouthernBiotech, USA), and coverslipped.

Confocal Microscopy and Image Analysis for Mouse Cochleae

The lengths of mouse cochlear pieces were measured and a cochlear frequency map was computed using a custom plug-into ImageJ. Following the frequency map, cochlear structures were located to relevant frequency regions. Using a confocal microscope (Leica SP8 AOBS), OHC and IHC zones were imaged in each case at four frequency locations (10, 20, 28.3 and 40 kHz) with a high-resolution, oil-immersion objective (100×, numerical aperture 1.0) with two digital zooms.

The quantification of OHCs was evaluated in the field of total 12 IHCs at each frequency locations with 1.0 digital zoom, so the maximum number of OHCs recorded was 36. OHC survival was calculated as percentage present divided by the normal number of OHCs. For IHC ribbon synapse quantification, 3D (x-y-z axis) images were scanned with 2.0 digital zoom, by a step size of 0.15 mm on z axis. Displaying spatial staining, images of z-stacks were three-dimensionally produced by Leica Microsystems LAS AF. Immunostained presynaptic CtBP2 (red) was counted as a ribbon synapse. Synaptic ribbons of ten consecutive IHCs distributed at each of the 10, 20, 28.3 and 40 kHz areas were calculated. The synaptic ribbons in the normal cochlear were also calculated using the same method to serve as control comparison samples. Thus, synaptic ribbon survival in noise-exposed mice was calculated as number of ribbons in a noise-exposed sample divided by the mean number of ribbons in the un-exposed, normal cochlear samples.

Statistical Analyses

ABR threshold shifts, P1 amplitudes, DPOAE amplitudes, HC losses, and ribbon synapse losses were all compared between groups with two-way ANOVAs.

Effect of Different Doses of TET on ABR Thresholds in the Mouse

Figure 9A:
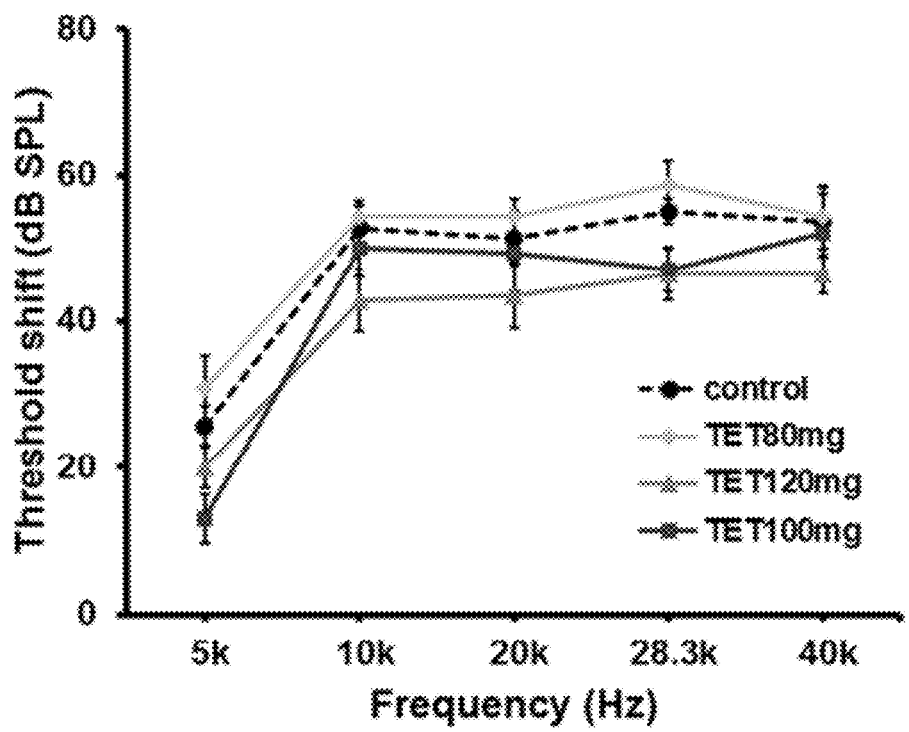
FIGS. 9A and 9B illustrate the noise-induced ABR threshold shift in mice with different doses of protective TET.
Figure 9B:
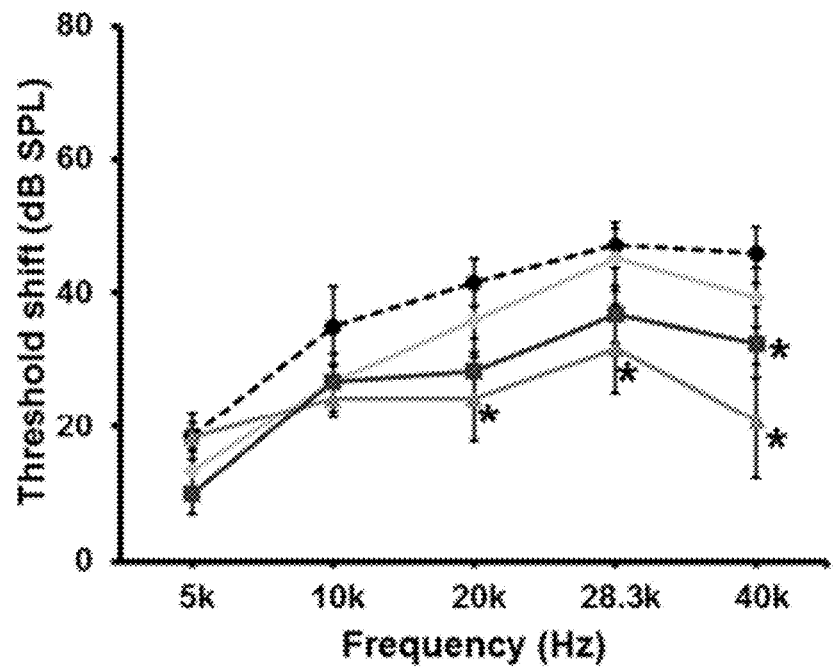

Noise-induced ABR threshold shifts were obtained by the comparison of the post-exposure thresholds with the pre-exposure ones. In the mouse, TET doses of 80, 100, and 120 mg/kg were used to show the dose-dependent effect on NIHL. FIG. 9A showed the mean threshold shift at Day 1 and FIG. 9B displayed mean threshold shifts at Day 15. A three-factor ANOVA (group×frequency×day) revealed a significant two-way interaction of group×day [$F(3,115)=3.465$, $p=0.019$]. One-way ANOVAs at each day revealed significant main effects of group at Day 1 [$F(3,154)=4.642$, $p=0.0.004$] and Day 15 [$F(3,134)=6.587$, $p<0.001$]. Tukey A pairwise comparisons revealed that the TET120 group had lower threshold shifts than the control ($p=0.018$) and TET80 ($p=0.013$) groups at Day 1, and that the TET100 ($p=0.009$) and TET120 ($p<0.001$) groups had lower threshold shifts than the control group at Day 15.

Preventive and Therapeutic Effect of TET on ABR

Figure 10A:
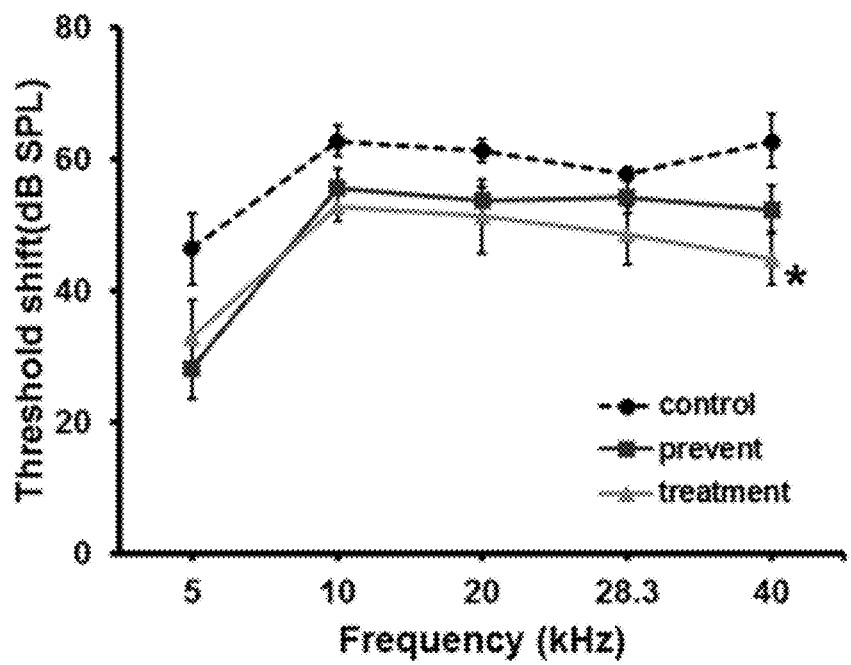
FIGS. 10A and 10B illustrate the preventive and therapeutic effects of TET on ABR in mice. In the prevent group, TET was injected 2 hours before noise exposure. In the treatment group, TET was injected after noise exposure.
Figure 10B:
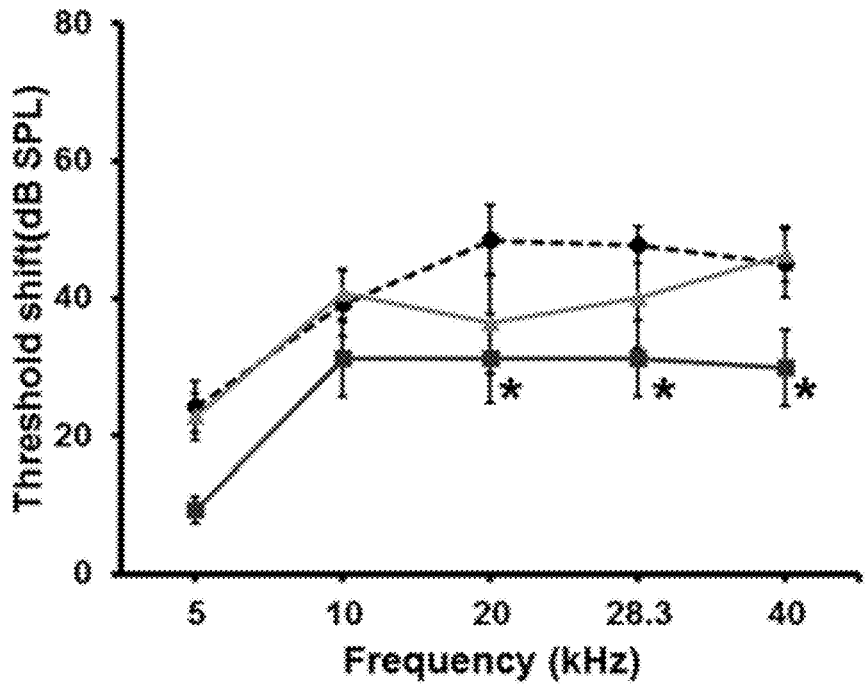

A TET dose of 120 mg/kg was administered in a single dose either before ('prevent' group) or after ('treatment' group) noise exposure in order to compare the two effects. FIG. 10A shows the threshold at Day 1 of the prevent and treatment groups, and FIG. 10B displays threshold shift at Day 15. A three-factor ANOVA (group×frequency×day) revealed a significant two-way interaction of group×day [F(2,95)=8.361, p<0.001]. One-way ANOVAs at each day revealed significant main effects of group at Day 1 [F(2, 109)=9.017, p<0.001] and Day 15 [F(2,109)=8.883, p<0.001]. Tukey A pairwise comparisons revealed that both the prevent (p=0.003) and treatment (p<0.001) groups had lower threshold shifts than the control group at Day 1, and that the prevent group had lower threshold shifts than the control (p<0.001) and treatment (p=0.010) groups at Day 15.

Preventative Effect of TET on Noise-Induced DPOAE Changes

Figure 11:
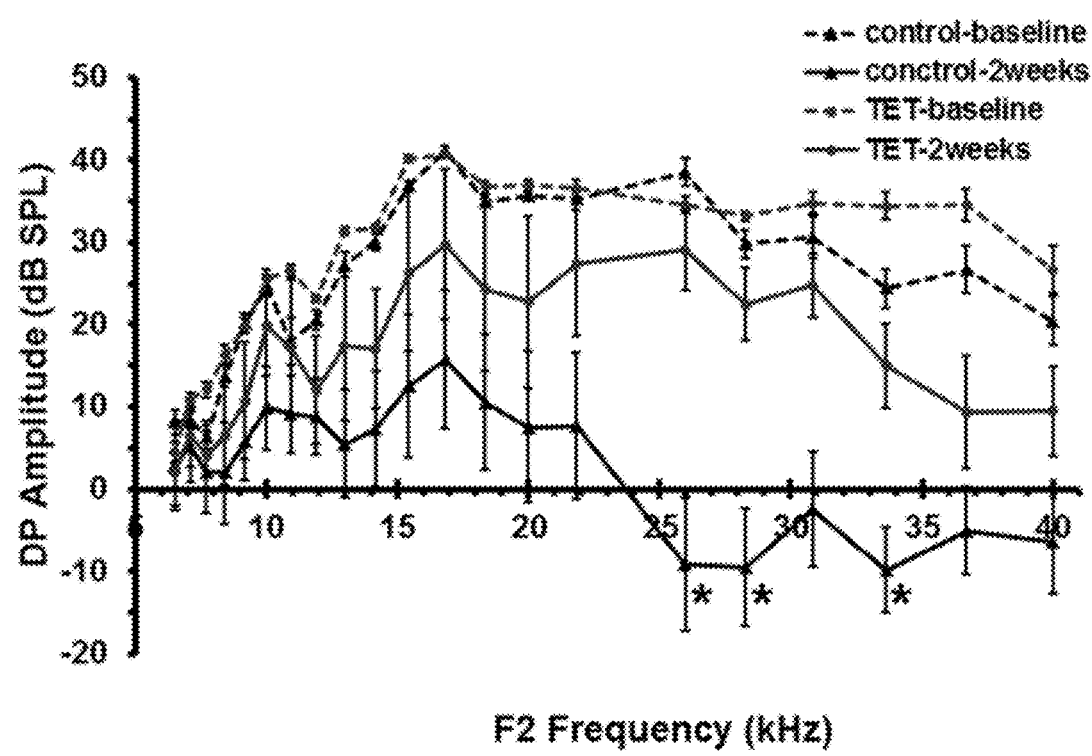
FIG. 11 illustrates the DPOAE amplitudes at the f2 frequencies in the control and TET prevent groups before and at Day 15 after noise exposure in mice. DPOAE amplitudes in the prevent group were significantly higher than the control group's at Day 15. Values are means±SEM. (n=7-8 per group). (*$p<0.05$, **$p<0.01$, compared to control, two-way ANOVA).

The DPOAE amplitudes at each f2 frequency in the control and TET prevent groups are displayed in FIG. 11. A three-factor ANOVA (group×frequency×day) was used to compare pre-exposure amplitudes to Day 15 amplitudes. The ANOVA revealed a significant two-way group×day interaction (F(1,40)=7.769, p=0.008). Independent samples t-tests were then used to compare the control and the prevent groups at pre-exposure and Day 15. Pre-exposure amplitudes were not significantly different, but Day 15 amplitudes were (T(46)=−3.367, p=0.002), indicating that the control group's amplitudes were significantly lower than the prevent group at Day 15 post noise.

Preventative Effect of TET on Noise-Induced ABR Wave-1 Amplitude Reductions

ABR wave-1 amplitude represents the summed activity of the cochlear nerve, and is known to be reduced in the noise-exposed mouse. FIG. 12A to D display mean wave-1 amplitudes at 10, 20, 28.3, and 40 kHz, respectively, in the control and TET prevent groups before noise and at Day 15 post noise. The mean data at 10 and 20 kHz indicate that the TET prevent group recovered by Day 15 to near pre-exposure amplitudes, whereas incomplete recovery was found in control group. At the higher frequencies (28.3 and 40 kHz), ABR wave-1 amplitudes were partially recovered in the TET prevent group compared to the pre-exposure baselines. Amplitudes from the 35-90 dB SPL stimuli were compared between groups in the pre-noise test using a three-factor ANOVA (group×frequency×stimulus level), and no group differences were detected. At Day 15, only the 50-90 dB SPL stimulus levels were used because many of the subjects had no responses below 50 dB SPL. The three-factor ANOVA revealed a significant two-way interaction of group×stimulus level [F(8, 232)=3.458, p=0.001]. Independent samples t-tests revealed that the TET prevent group had higher amplitudes across frequencies at 50-60 dB SPL and 70-90 dB SPL.

Quantitative Assessment of OHCs and Ribbon Synapses

Figure 13A:
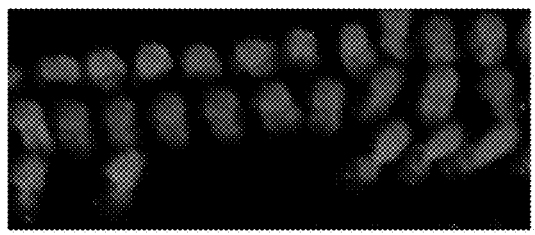
FIGS. 13A, 13B, 13C, and 13D illustrate the representative images of immunostaining and confocal imaging from mouse cochlear samples showing the OHCs and IHC ribbon synapses at Day 15 after noise exposure.
Figure 13B:
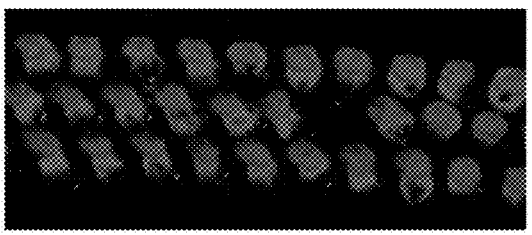
Figure 13C:
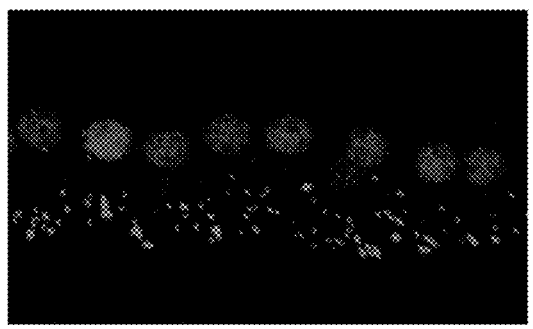
Figure 13D:
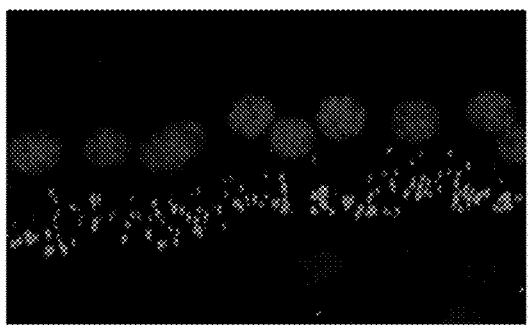
Figure 14A:
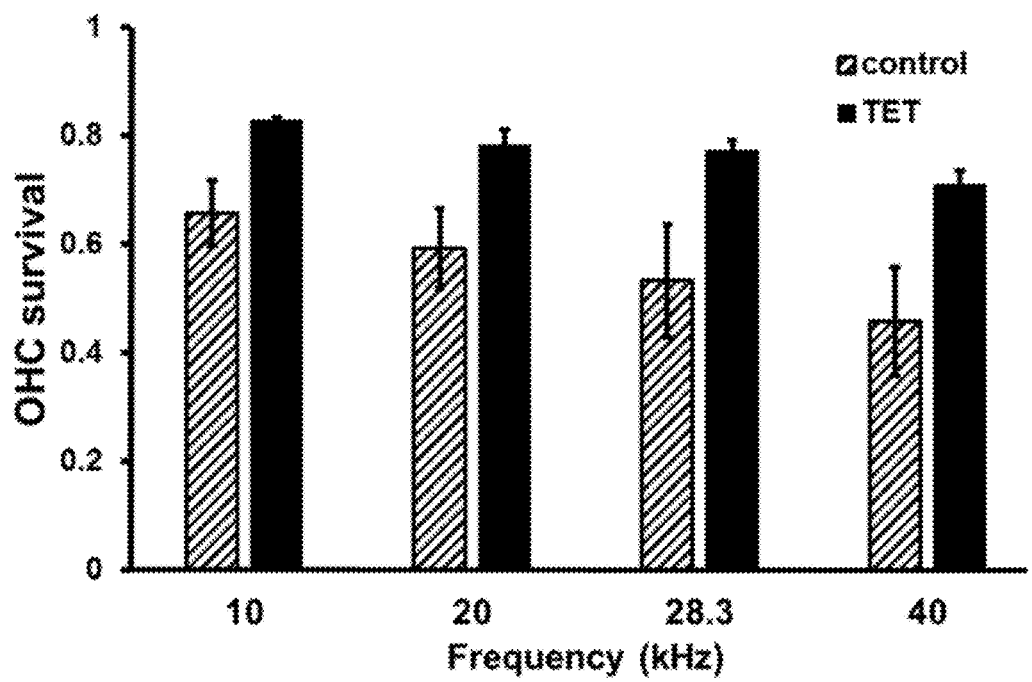
FIGS. 14A and 14B illustrate the quantitative assessment of OHCs and IHC ribbon synapses in the mouse control and TET prevent groups. Proportions of OHC and synapse ribbon survival were calculated as the number of counted cells/synapses divided by the numbers in normal uninjured cochlea samples.
Figure 14B:
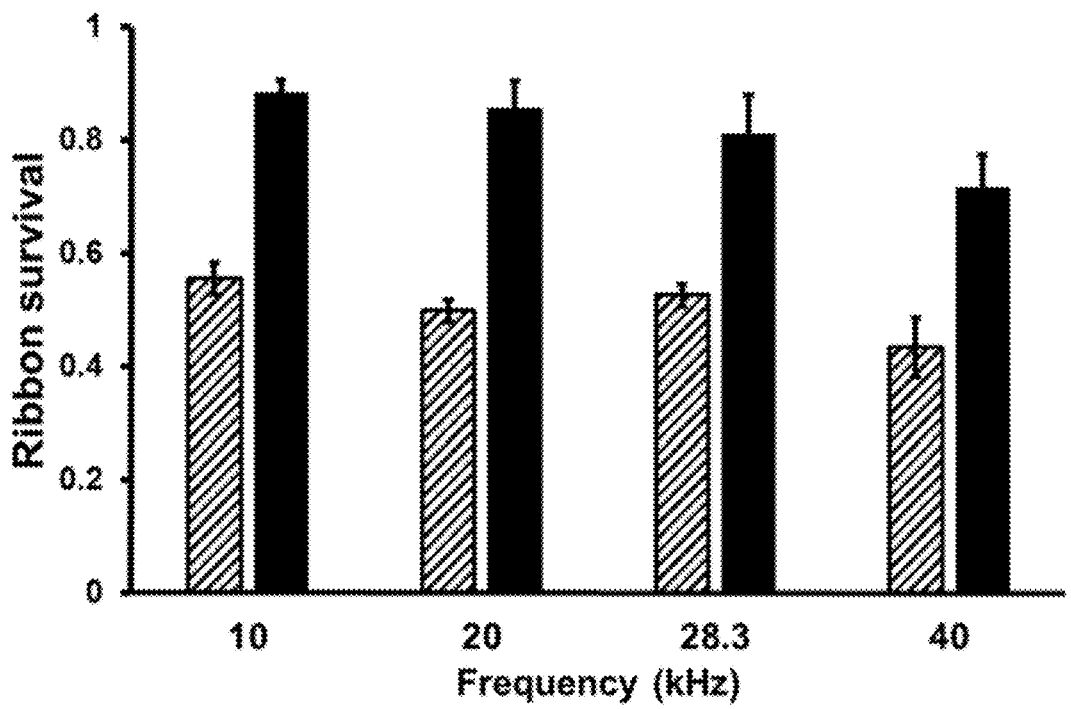

At the end of the experiments, cochlear samples were collected for analysis of noise-induced injury. Surviving OHCs and IHC ribbon synapses were counted. Representative samples of the mouse OHC, IHC, and ribbon synapse visualization are displayed in FIG. 13A to D. OHCs and IHC ribbon synapses were aggregated in sections of the basilar membrane tuned to the test frequencies assessed with the ABR. Quantitative data are displayed in FIGS. 14A and 14B, respectively. Two-factor ANOVAs (group×frequency) were used compare the number of surviving OHCs and intact ribbon synapses between groups. For the mouse OHC loss, the TET prevent and control groups were compared. OHC loss was significant more severe in control group than in the TET prevent group (FIGS. 13A and 13B). The two-factor ANOVA revealed a significant two-way interaction [F(4,40)=2.854, p=0.036]. Independent samples t-tests at each frequency revealed that the proportion of surviving OHCs was higher in the TET prevent group at the regions tuned to 10, 20, 28.3, and 40 kHz (FIG. 14A). To assess the protection of the ribbon synapses, the cochlear samples were immunostained with CtBP2, one of the most abundant proteins in synaptic ribbon bodies (FIGS. 13C and 13D). The ANOVA revealed another two-way interaction [F(4,40)=4.804, p=0.003]. Independent samples t-tests at each frequency revealed that the TET prevent group had more synaptic ribbon survival than the control group at the 10, 20, 28.3, and 40 kHz regions (FIG. 14B).

Example 12: TET Reduces Behavioral Indications of Tinnitus in Mice

This example demonstrated that TET can significantly diminish salicylate and noise induced tinnitus-like behavior in mice, using the sound based avoidance detection (SBAD) method.

Behavioral Test

The SBAD method with Go/No-Go paradigm was used for behavioral test in mice. For "Go" trial animals were trained to move from one compartment to another upon presentation of a sound. For "No-Go" trial animals were trained to stay in the compartment. Otherwise they received a shock. "Go" paradigm was used to monitor motor, motivation, and memory functions while "No-Go" was used to detect tinnitus-like behavior.

Salicylate-Induced Tinnitus Model

A baseline was established for each mouse over three consecutive days. The same SBAD method was repeated one hour after intraperitoneal injections of sodium salicylate (400 mg/kg), and two hours after TET injections.

In the salicylate model, TET diminished tinnitus-like behavior (FIGS. 15A to D). FIGS. 15A&15B: Go/No-Go correct rate for both male and female mice. FIG. 15C: No significant changes for the "Go" testing either before or after drug injections, indicating that salicylate and TET have no obvious effects on motor, motivation or memory functions at these dosages. FIG. 15D: TET significantly decreased behavioral indications of tinnitus at a dosage of 10 and 30 mg/kg, but no significant changes were observed at a 5 mg/kg dosage, a positive dose effect correlation. Paired t test was used for statistical analysis. Compared with Baseline, **P<0.01.

Noise-Induced Tinnitus Model

One ear was exposed to a 120 dB noise (4-25 kHz) for two hours for this noise-induced tinnitus model. DPOAE and ABR were measured to monitor possible hearing loss in each ear 2 weeks after noise exposure. SBAD measurements were made 2, 4, and 8 weeks after noise exposure, and also after TET (0, 30, 60, 90 mg/kg) injection.

Figure 16A:
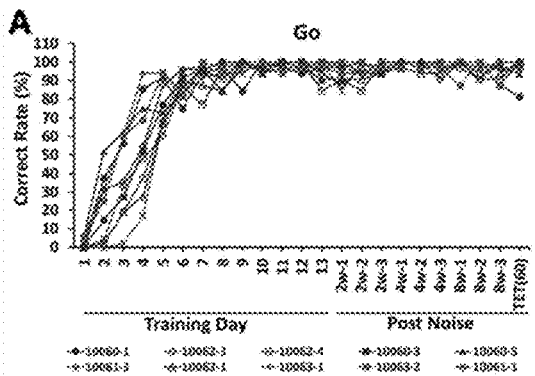
FIGS. 16A, 16B, 16C, and 16D illustrate that TET also diminished tinnitus-like behavior in the noise model.
Figure 16B:
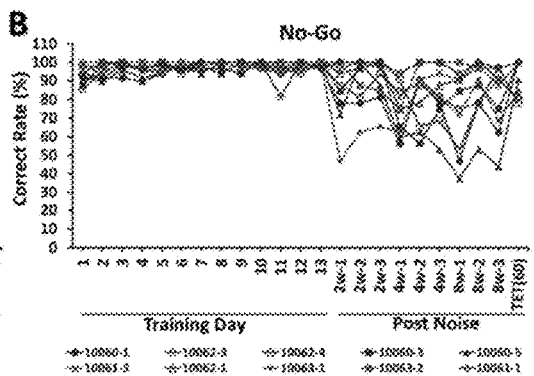
Figure 16C:
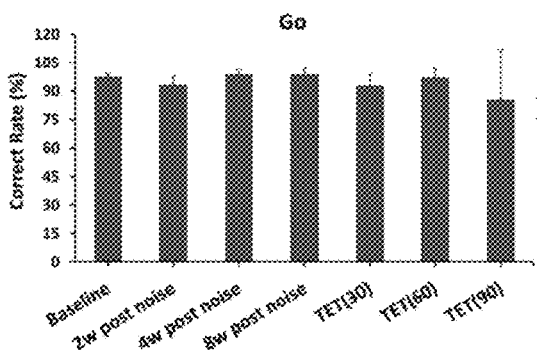
Figure 16D:
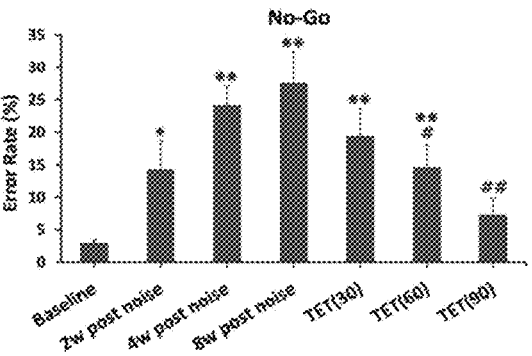

In the noise model, TET also diminished tinnitus-like behavior (FIGS. 16A to D). FIGS. 16A&16B: Go/No-Go correct rate for TET (60 mg/kg) group mice. FIG. 16C: No significant changes were observed for the "Go" trials. FIG. 16D: TET significantly decreased behavioral indications of tinnitus at a dosage of 60 and 90 mg/kg, but no significant changes were observed at a 30 mg/kg dosage, another positive dose effect correlation. Paired t test was used for statistical analysis. Compared with Baseline, *P<0.05, **P<0.01; compared with 8w post noise, #P<0.05, ##P<0.01.

Example 13: Determine the Effect of TET Combination Treatment for NIHL

Materials and methods will be similar to the examples above. TET powder will be dissolved in 0.01 M hydrogen chloride (HCl), and the pH will be adjusted to 6.5 with 0.01

M Sodium hydroxide (NaOH). The control solution will be made with HCL and NaOH, and the pH will be adjusted to 6.5. The mice will be exposed to noise and will be randomized into 26 groups with both genders: 24 drug groups and 2 control groups. The 24 drug groups will be: 1) TET+allopurinol; 2) TET+glutathione; 3) TET+allopurinol; 4) TET+L-carnitine; 5) TET+methionine; 6) TET+riluzole; 7) TET+caroverine; 8) TET+memantine; 9) TET+magnesium; 10) TET+fluoxetine; 11) TET+sertraline; 12) TET+S-citalopram; 13) TET+alaproclate; 14) TET+amantadine; 15) TET+bifemelane; 16) TET+pirlindole; 17) TET+milnacipran; 18) TET+bicifadine; 19) TET+nimodipine; 20) TET+verapamil; 21) TET+atomoxetine; 22) TET+indeloxazine; 23) TET+zonisamide; and 24) TET+gabapentin. The 2 control groups will be the prevent group and the treatment group. For the drug groups, the mice will be injected once per day for five consecutive days: two days before noise exposure, the day of the noise exposure, and two days after with 120 mg/kg TET per injection. Two control groups will be treated with one or five vehicle injections over the same schedules as the drug groups.

The ABR and DPOAE data for all the groups will be collected and analyzed. The result will demonstrate that the treatment of TET and another active pharmaceutical ingredient (API) will attenuate noise-induced hearing loss in rodent model of NIHL.

While some embodiments have been shown and described herein, such embodiments are provided by way of example only. Numerous variations, changes, and substitutions will now occur to those skilled in the art without departing from the invention. It should be understood that various alternatives to the embodiments of the invention described herein can be employed in practicing the invention.

What is claimed is:

1. A method for treating noise induced hearing loss in a subject in need thereof comprising administering a therapeutically effective amount of tetrandrine (TET) or a salt thereof.

2. The method of claim 1, wherein the subject is a human.

3. The method of claim 1, wherein the subject is suffering from the noise induced hearing loss.

4. The method of claim 1, wherein the method treats the noise induced hearing loss.

5. The method of claim 1, wherein the subject is at risk of developing the noise induced hearing loss.

6. The method of claim 1, wherein the subject is diagnosed with the noise induced hearing loss.

7. The method of claim 1, wherein the method delays onset of the noise induced hearing loss.

8. The method of claim 1, wherein the therapeutically effective amount of TET or salt thereof is administered orally, auricularly, intratympanically, buccally, intravenously, parenterally, rectally, intradermally, transdermally, pulmonary, nasally, topically, or by inhalation spray.

9. The method of claim 8, wherein the therapeutically effective amount of TET or salt thereof is administered auricularly.

10. The method of claim 9, wherein the auricular administration is an injection.

11. The method of claim 9, wherein the auricular administration is an eardrop.

12. The method of claim 1, wherein the therapeutically effective amount of TET or salt thereof is at least about 1 µg of TET or salt thereof per kg of the subject.

13. The method of claim 1, wherein the therapeutically effective amount of TET or salt thereof is less than about 1000 mg of TET or salt thereof per kg of the subject.

14. The method of claim 1, wherein the therapeutically effective amount of TET or salt thereof is from about 1 µg to about 1000 mg of TET or salt thereof per kg of the subject.

15. The method of claim 1, wherein the therapeutically effective amount of TET or salt thereof is comprised in a pharmaceutical composition.

16. The method of claim 1, wherein the therapeutically effective amount of TET or salt thereof is in a unit dosage form.

17. The method of claim 16, wherein the unit dosage form is administered at least once a day, twice a day, or three times a day.

18. The method of claim 16, wherein the unit dosage form is administered for at least one day, at least two days, at least three days, at least four days, at least five days, at least six days, at least one week, at least two weeks, at least three weeks, at least four weeks, at least one month, at least two months, at least six months, or at least one year.

19. The method of claim 16, wherein the unit dosage form is administered intermittently.

20. The method of claim 16, wherein the unit dosage form is administered continuously.

21. The method of claim 16, wherein the unit dosage form is in a tablet, capsule, caplet, gel cap, powder, or solution dosage form.

22. The method of claim 21, wherein the tablet, capsule, caplet, gel cap, powder, or solution dosage form has a unit weight of at least about 10 mg.

23. The method of claim 21, wherein the tablet, capsule, caplet, gel cap, powder, or solution dosage form has a unit weight of less than about 10 g.

24. The method of claim 21, wherein the tablet, capsule, caplet, gel cap, powder, or solution dosage form has a unit weight of from about 10 mg to about 10 g.

25. The method of claim 1, wherein the therapeutically effective amount of TET or salt thereof is in a solution dosage form.

26. The method of claim 25, wherein the solution dosage form has a unit volume of at least about 1 mL.

27. The method of claim 25, wherein the solution dosage form has a unit volume of less than about 500 mL.

28. The method of claim 25, wherein the solution dosage form has a unit volume of from about 1 mL to about 500 mL.

29. The method of claim 1, wherein the therapeutically effective amount of TET or salt thereof is in a powder dosage form.

30. The method of claim 29, further comprising mixing a sterile solution with the powder dosage form prior to the administration of the therapeutically effective amount of TET or salt thereof.

31. The method of claim 1, wherein the therapeutically effective amount of TET or salt thereof is administered at least about 12 hours before occurrence of the noise induced hearing loss or an event that initiates the noise induced hearing loss.

32. The method of claim 1, wherein the therapeutically effective amount of TET or salt thereof is administered less than about 10 days before occurrence of the noise induced hearing loss or an event that initiates the noise induced hearing loss.

33. The method of claim 1, wherein the therapeutically effective amount of TET or salt thereof is administered at least about 12 hours after occurrence of the noise induced hearing loss or an event that initiates the noise induced hearing loss.

34. The method of claim 1, wherein the therapeutically effective amount of TET or salt thereof is administered less than about 10 days after occurrence of the noise induced hearing loss or an event that initiates the noise induced hearing loss.

35. The method of claim 1, wherein the therapeutically effective amount of TET or salt thereof is in a supplement product.

36. The method of claim 1, wherein the therapeutically effective amount of TET or salt thereof is comprised in an herb extract.

37. The method of claim 36, wherein the herb is *Stephania tetrandra*.

38. The method of claim 36, wherein the herb is *Stephania tetrandra* S Moore.

39. The method of claim 1, wherein the therapeutically effective amount of TET or salt thereof is isolated and purified.

40. The method of claim 1, wherein the therapeutically effective amount of TET or salt thereof is a diastereoisomer having a diastereomeric excess of at least about 50%, at least about 60%, at least about 70%, at least about 80%, at least about 85%, at least about 90%, at least about 95%, or from at least about 50% to about 100%.

41. A method for treating noise induced hearing loss in a subject in need thereof comprising administering a pharmaceutical composition that comprises a therapeutically effective amount of tetrandine (TET) or a salt thereof and an active pharmaceutical ingredient (API) or a salt thereof.

42. The method of claim 41, wherein the therapeutically effective amount of TET or salt thereof is administered orally, auricularly, intratympanically, buccally, intravenously, parenterally, rectally, intradermally, transdermally, pulmonary, nasally, topically, or by inhalation spray.

43. The method of claim 41, wherein the therapeutically effective amount of TET or salt thereof and the API or salt thereof are administered concurrently.

44. The method of claim 41, wherein the therapeutically effective amount of TET or salt thereof and the API or salt thereof are administered consecutively.

45. The method of claim 41, wherein the API or salt thereof is administered in a different route as the therapeutically effective amount of TET or salt thereof.

* * * * *